United States Patent
Hendrix et al.

(10) Patent No.: US 7,488,733 B2
(45) Date of Patent: Feb. 10, 2009

(54) 6-ARYLAMINO-5-CYANO-4-PYRIMIDINONES AS PDE9A INHIBITORS

(75) Inventors: Martin Hendrix, Odenthal (DE); Lars Bärfacker, Oberhausen (DE); Bettina Beyreuther, Düsseldorf (DE); Ulrich Ebert, Mannheim (DE); Christina Erb, Kriftel (DE); Frank-Thorsten Hafner, Wuppertal (DE); Heike Heckroth, Wuppertal (DE); Yan-Hong Liu, Frankfurt (DE); Dagmar Karthaus, Solingen (DE); Adrian Tersteegen, Wuppertal (DE); Franz-Josef van der Staay, Dronten (NL); Marja van Kampen, Düsseldorf (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/559,954

(22) PCT Filed: Jun. 16, 2004

(86) PCT No.: PCT/EP2004/006477

§ 371 (c)(1),
(2), (4) Date: Sep. 28, 2006

(87) PCT Pub. No.: WO2004/113306

PCT Pub. Date: Dec. 29, 2004

(65) Prior Publication Data

US 2007/0105881 A1    May 10, 2007

(30) Foreign Application Priority Data

Jun. 25, 2003   (DE) ................. 103 28 479

(51) Int. Cl.
*C07D 239/42*   (2006.01)
*C07D 401/12*   (2006.01)
*A61K 31/505*   (2006.01)

(52) U.S. Cl. ...................... 514/269; 544/319
(58) Field of Classification Search ............. 544/319; 514/269
See application file for complete search history.

(56) References Cited

U.S. PATENT DOCUMENTS

| | | | |
|---|---|---|---|
| 3,732,225 | A | 5/1973 | Breuer et al. |
| 5,002,949 | A | 3/1991 | Peseckis et al. |
| 5,256,668 | A | 10/1993 | Hsu et al. |
| 5,656,629 | A | 8/1997 | Bacon et al. |
| 5,977,118 | A | 11/1999 | Bacon et al. |
| 2004/0266736 | A1 | 12/2004 | Wunder et al. |
| 2006/0100222 | A1 | 5/2006 | Boss et al. |
| 2006/0106035 | A1 | 5/2006 | Hendrix et al. |
| 2006/0111372 | A1 | 5/2006 | Hendrix et al. |
| 2007/0105876 | A1 | 5/2007 | Hendrix et al. |
| 2007/0161662 | A1 | 7/2007 | Hendrix et al. |

FOREIGN PATENT DOCUMENTS

| | | |
|---|---|---|
| CA | 2 283 211 A1 | 9/1998 |
| CA | 2 438 890 A1 | 9/2002 |
| CA | 2 417 631 A1 | 1/2003 |
| CA | 2 484 997 A1 | 11/2003 |
| CA | 2 496 194 A1 | 3/2004 |
| CA | 2 496 292 A1 | 4/2004 |
| CA | 2 496 308 A1 | 4/2004 |
| CH | 396 924 | 8/1965 |
| CH | 396 925 | 8/1965 |
| CH | 396 926 | 8/1965 |
| CH | 396 927 | 8/1965 |
| DE | 1 147 234 | 4/1963 |
| DE | 1 149 013 | 5/1963 |
| DE | 1 156 415 | 10/1963 |
| DE | 2 408 906 | 2/1974 |
| DE | 101 56 249 A1 | 5/2003 |
| EP | 0 130 735 A1 | 1/1985 |
| EP | 0 995 751 A2 | 4/2000 |
| GB | 937726 | 9/1963 |
| WO | 95/10506 A1 | 4/1995 |
| WO | WO 98/10765 A1 | 3/1998 |
| WO | 98/40384 A1 | 9/1998 |
| WO | 99/41253 A1 | 8/1999 |
| WO | 00/18758 A1 | 4/2000 |
| WO | 02/06288 A1 | 1/2002 |
| WO | 02/09713 A2 | 2/2002 |
| WO | 02/055082 A1 | 7/2002 |
| WO | 02/068423 A1 | 9/2002 |

(Continued)

OTHER PUBLICATIONS

Vippagunta et al., Crystalline Solids, Advanced Drug Delivery Reviews, 48, pp. 3-26, 2001.*

(Continued)

*Primary Examiner*—Deepak Rao
(74) *Attorney, Agent, or Firm*—Michael P. Morris; Mary-Ellen M. Devlin; Edouard G. Lebel

(57) ABSTRACT

The invention relates to novel 6-arylamino-5-cyano-4-pyrimidinones of formula (I)

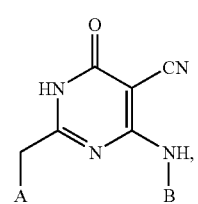

methods for the production thereof, and the use thereof for producing medicaments utilized for improving awareness, concentration, learning capacity, and/or retentiveness of memory. Said compounds (I) show activity as PDE9 inhibitors.

8 Claims, No Drawings

FOREIGN PATENT DOCUMENTS

| | | |
|---|---|---|
| WO | 02/098864 A1 | 12/2002 |
| WO | 03/041725 A2 | 5/2003 |
| WO | WO 03/037899 A1 | 5/2003 |
| WO | 03/093269 A2 | 11/2003 |
| WO | 2004/018474 A1 | 3/2004 |
| WO | 2004/026286 A1 | 4/2004 |
| WO | 2004/026876 A1 | 4/2004 |

OTHER PUBLICATIONS

West, Solid Solutions, Chapter 10, pp. 358 and 365, 1988.*
Ulrich, Crystallization: 4. Crystal Characteristics, Kirk-Othmer Encyclopedia of Chemical Technology, Aug. 2002.*
Lugnier, Cyclic nucleotide PDE Superfamily, Pharmacology & Therapeutics 109, pp. 366-398, 2006.*
Bagli, J., et al., "Chemistry and Positive Inotropic Effect of Pelrinone and Related Derivatives. A Novel Class of 2-Methylpyridinones as Inotropic Agents", J. Med. Chem., 31(4): 814-823 (1988).
International Search Report for corresponding international application PCT/EP2004/006477 mailed Oct. 27, 2004.
International Search Report for PCT/03/08923 mailed Dec. 15, 2003.
International Search Report for PCT/EP03/08979 mailed Nov. 25, 2003.
International Search Report for PCT/EP03/08880 mailed Apr. 16, 2004.
International Search Report for PCT/EP2004/004412 mailed Jul. 14, 2004.
International Search Report for PCT/EP2004/004455 mailed Sep. 17, 2004.
International Search Report for PCT/EP2004/014872 mailed May 19, 2005.
Ji-Ye Wei, et al; Molecular and Pharmacological Analysis of Cyclic Nucleotide-Gated Channel Function in the Central Nervous System, Progress in Neurobiology (1998) vol. 56, pp. 37-64.
Douglas A. Fisher, et al; Isolation and Characterization of PDE8A, A Novel Human cGMP-specific Phosphodiesterase; Journal of Biological Chemistry (1998) vol. 273, No. 25, pp. 15559-1 5564.
Michel Guipponi, et al; Identification and Characterization of a Novel Cydic Nudeotide Phosphodiesterase Gene (PDE8A) That Maps to 21q22.3: Alternative Splicing of mRNA Transcripts, Genomic Structure and Sequence; Hum Genet (1998) vol. 103, pp. 386-392.
Scott H. Sonderling, et al; Identification and Characterization of a Novel Family of Cyclic Nucleotide Phosphodiesterases, Journal of Biological Chemistry (1998) vol. 273, No. 25, pp. 15553-15558.
Svetlana G. Andreeva, et al; Expression of cGMP-Specific Phosphodiesterase 9A mRNA in the Rat Brain, Journal of Neuroscience (2001) vol. 21, No. 22, pp. 9068-9076.
Timothy J. Martins, et al; Purification and Characterization of a Cydic GMP-stimulated Cyclic Nucledide Phosphodiesterase from Bovine Tissues, Journal of Biological Chemistry (1982) vol. 257, No. 4, pp. 1973-1979.
Sharron H. Francis, et al; Characterization of a Novel cGMP Binding Protein from Rat Lung, Journal of Biological Chemistry (1980) vol. 255, No. 2, pp. 620-626.
Peter G. Gillespie, et al; Characterization of a Bovine Cone Photoreceptor Phosphodiesterase Purified by Cydic GMP-Sepharose Chromatography; Journal of Biological Chemistry (1988) vol. 263. No. 17, pp. 8133-8141.
Lindsay Fawcett, et al; Molecular Cloning and Characterization of a Distinct Human Phosphodiesterase Gene Family: PDE1 1A; Proc. Natl. Acad. *Sci.* (2000) vol. 97, No. 7, pp. 3702-3707.
Seiko Murashima, et al; Characterization of Particulate Cyclic Nucleotide Phosphodiesterases from Bovine Brain: Purification of a Distinct cGMP-Stimulated Isoenzyme; Biochemistry (1990) vol. 29, No. 22 pp. 5285-5292.
Scott H. Sonderling, et al; Regulation of CAMP and cGMP signaling: new phosphodiesterases and new functions; Current Opinion in Cell Biology (2000) vol. 12, pp. 174-179.
Akira Miyashita, et al; Studies on Pyrazolo[3,4-d]Pyrimidine Derivatives. XVIII. Facile Preparation of 1H-Pyrazolo[3,4-d]Pyrimidin-4(5H)-Ones; Heterocycles (1990) vol. 31, No. 7, p. 1309-1314.
Kate Loughney, et al; Isolation and Characterization of cDNAs Corresponding to Two Human Calcium, Calmodulin-regulated. 3',5'-Cyclic Nucleotide Phosphodiesterases, Journal of Biological Chemistry (1996) vol. 271, No. 2, pp. 796-806.
Guy J. Rosman, et al; Isolation and Characterization of Human cDNAs encoding a cGMPstimulated 3',5'-Cyclic Nucleotide Phosphodiesterase; Gene (1997) vol. 191, pp. 89-95.
Takashi Miki, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.
Rena Obernolte, et al; The cDNA of a Human Lymphocyte cyclic-AMP Phosphodiesterase (PDE IV) Reveals a Multigene Family; Gene (1993) vol. 129, pp. 239-247.
Kate Loughney, et al; Isolation and Characterization of cDNAs encoding PDE5A, a Human cGMP-Binding, cGMP-Speafic Y.9-Cydic Nudeotide Phosphodiesterase; Gene (1998) vol. 216, pp. 139-147.
J. M. Hetman, et al; Cloning and Characterization of PDE7B, a CAMP-specific Phosphodiesterase, Proc. Natl. Acad. Sci. (2000) vol. 97, No. 1, pp. 472-476.
Douglas A. Fisher, et al; Isolation and Characterization of PDEM, a Novel Human CAMP-Specific Phosphodiesterase; Biochemical and Biophysical Research Communications (1998) vol. 246, pp. 570-577.
Kotomi Fujishige, et al; Cloning and Characterization of a Novel Human Phosphodiesterase That Hydrolyzes R21 Both CAMP and cGMP (PDE10A); Journal of Biological Chemistry (1999) vol. 274, No. 26, pp. 18438-.18445.
James E. Huettner, et al; Primary Culture of Identified Neurons from the Visual Cortex of Postnatal Rats; Journal of Neuroscience (1986) vol. 6, pp. 3044-3060.
Magnus Roenn, et al; Palladium (II)-Catalyzed Cyclization Using Molecular Oxygen as Reoxidant; Tetrahedron Letters (1995) vol. 36, No. 42, pp. 7749-7752.
C. C. Cheng, et al; Potential Purine Antagonists VII. Synthesis of 6-Alkylpyrazolo-[3,4-d]pyrimidines; Journal of Organic Chemistry (1958) vol. 23 pp. 191-200.
Hieke Gielen, et al; A Novel Approach to Amidines from Esters; Tetrahedron Letters (2002) vol. 43 pp. 419-421.
K. Hemender Reddy, et al; Versatile Synthesis of 6-Alkyl/Aryl-1H-Pyrazolo[3,4-d]Pyrimidin-4[5H]-Ones; Indian Journal of Chemistry (1992) vol. 31B, pp. 163-166.
Arne Schousboe, et al; Role of Ca++ and Other Second Messengers in Excitatory Amino Acid Receptor Mediated Neuogeneration: Clinical Perspective; Clinical Neuroscience (1997) vol. 4, pp. 194-198.
Rudolf Gompper, et al; Substituted Dithiocarboxylic Acids and Ketene Thioacetals; Institute for Organic Chemistry Technology (1962) vol. 95, pp. 2861-2870. German & English Translation.
P. Schmidt, et al; A New Synthesis of Pyrazolo [3,4-d] Pyrimidines Having Coronary Dilation Properties; Helvetica Chimica Acta (1962) vol. XLV, No. 189, pp. 1620-1627. German & English Translation.
Accessed on Mar. 18, 2007. http://www.mentalhealth.org.uk/information/mental-health-a-z/dementia.
Jehan Bagli, et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

* cited by examiner

6-ARYLAMINO-5-CYANO-4-PYRIMIDINONES AS PDE9A INHIBITORS

This application is a 371 of PCT/EP2004/006477, filed Jun. 16, 2004, which claims the benefit of German application 10 328 479.6 filed Jun. 25, 2003.

The invention relates to novel 6-arylamino-5-cyano-4-pyrimidinones, process for their preparation, and the use thereof for producing medicaments for improving perception, concentration, learning and/or memory.

Inhibition of phosphordiesterases modulates the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56: 37-64). The phosphodiesterases (PDE) are a control mechanism for controlling the activity of cAMP and cGMP and thus in turn these physiological processes. PDEs hydrolyze the cyclic monophosphates to the inactive monophosphates AMP and GMP. At least 21 PDE genes have now been described (*Exp. Opin. Investig. Drugs* 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A).

With a Michaelis-Menten constant (Km) of 170 nM, PDE9A has high affinity for cGMP. In addition, PDE9A is selective for cGMP (Km for cAMP=230 μM). PDE9A has no cGMP binding domain, suggesting allosteric enzyme regulation by cGMP. It was shown in a Western blot analysis that PDE9A is expressed in humans inter alia in the testes, brain, small intestine, skeletal muscle, heart, lung, thymus and spleen. The highest expression was found in the brain, small intestine, heart and spleen (Fisher et al., *J. Biol. Chem.*, 1998, 273 (25): 15559-15564). The gene for human PDE9A is located on chromosome 21q22.3 and comprises 21 exons. To date, 4 alternative splice variants of PDE9A have been identified (Guipponi et al., *Hum. Genet.*, 1998, 103: 386-392). Classical PDE inhibitors do not inhibit human PDE9A. Thus, IBMX, dipyridamole, SKF94120, rolipram and vinpocetine show no inhibition on the isolated enzyme in concentrations of up to 100 μM. An $IC_{50}$ of 35 μM has been demonstrated for zaprinast (Fisher et al., *J. Biol. Chem.*, 1998, 273 (25): 15559-15564).

Murine PDE9A was cloned and sequenced in 1998 by Soderling et al. (*J. Biol. Chem.*, 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 μM either; the $IC_{50}$ for zaprinast is 29 μM (Soderling et al., *J. Biol. Chem.*, 1998, 273 (19): 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22): 9068-9076). The hippocampus, cortex and basal forebrain in particular play an important role in learning and memory processes.

As already mentioned above, PDE9A is distinguished by having particularly high affinity for cGMP. PDE9A is therefore active even at low physiological concentrations, in contrast to PDE2A (Km=10 μM; Martins et al., *J. Biol. Chem.*, 1982, 257: 1973-1979), PDE5A (Km=4 μM; Francis et al., *J. Biol. Chem.*, 1980, 255: 620-626), PDE6A (Km=17 μM; Gillespie and Beavo, *J. Biol. Chem.*, 1988, 263 (17): 8133-8141) and PDE11A (Km=0.52 μM; Fawcett et al., *Proc. Nat. Acad. Sci.*, 2000, 97 (7): 3702-3707). In contrast to PDE2A (Murashima et al., *Biochemistry*, 1990, 29: 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12: 174-179). PDE9A inhibitors may therefore lead to an increase in the baseline cGMP concentration.

U.S. Pat. No. 5,256,668 discloses aminopyrimidine derivatives which are conspicuous as anti-viral agents and can be employed for the treatment of respiratory syncytial virus.

WO 99/41253 describes pyrimidine derivatives which have an antiviral effect and which can be employed in particular for the treatment of human cytomegalovirus infections.

EP 130735 discloses aminopyrimidine derivatives which are conspicuous as cardio-tonic agents.

The present invention relates to compounds of the formula

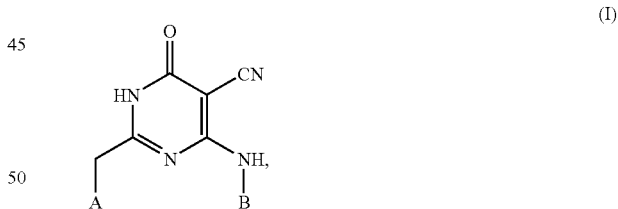

(I)

in which

A is $C_1$-$C_8$-alkyl, $C_3$-$C_8$-cycloalkyl, tetrahydrofuryl or tetrahydropyranyl, which are optionally substituted by up to 3 radicals independently of one another selected from the group of $C_1$-$C_6$-alkyl, $C_1$-$C_6$-alkoxy, hydroxycarbonyl, cyano, trifluoromethyl, trifluoromethoxy, amino, hydroxy, $C_1$-$C_6$-alkylamino, halogen, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio, where $C_1$-$C_6$-alkyl, $C_1$-$C_6$-alkoxy, $C_1$-$C_6$-alkylamino, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio are optionally substituted by one or more radicals selected from the group of hydroxy, cyano, halogen, hydroxycarbonyl and a group of the formula —NR³R⁴, where $R^3$ and $R^4$ are independently of one another hydrogen or $C_1$-$C_6$-alkyl, or $R^3$ and $R^4$ together with the nitrogen atom to which they are bonded are 5- to 8-membered heterocyclyl, B is phenyl or heteroaryl which are optionally substituted by up to 3 radicals independently of one another selected from the group of $C_1$-$C_6$-alkyl, $C_1$-$C_6$-alkoxy, hydroxycarbonyl, cyano, trifluoromethyl, trifluoromethoxy, amino, nitro, hydroxy, $C_1$-$C_6$-alkylamino, halogen, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio, where $C_1$-$C_6$-alkyl, $C_1$-$C_6$-alkoxy, $C_1$-$C_6$-alkylamino, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio are optionally substituted by a radical selected from the group of hydroxy, cyano, halogen, hydroxycarbonyl and a group of the formula —NR³R⁴, where $R^3$ and $R^4$ have the abovementioned meanings, and the salts, solvates and/or solvates of the salts thereof.

The compounds of the invention may, depending on their structure, exist in stereo-isomeric forms (enantiomers, diastereomers) and tautomeric forms. The invention therefore relates to the enantiomers or diastereomers and respective mixtures thereof. The stereoisomerically pure constituents can be isolated in a known manner from such mixtures of enantiomers and/or diastereomers.

Salts which are preferred for the purposes of the invention are physiologically acceptable salts of the compounds of the invention.

Physiologically acceptable salts of the compounds (I) include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Solvates refers for the purposes of the invention to those forms of the compounds which form, in the solid or liquid state, a complex by coordination with solvent molecules. Hydrates are a specific form of solvates in which the coordination takes place with water.

For the purposes of the present invention, the substituents have the following meaning, unless specified otherwise:

$C_1$-$C_8$-alkyl, $C_1$-$C_6$-alkyl, $C_1$-$C_5$-alkyl and $C_1$-$C_4$-alkyl are a straight-chain or branched alkyl radical having 1 to 8, preferably 1 to 6, particularly preferably 1 to 5 and 1 to 4 carbon atoms. Preferred examples include methyl, ethyl, n-propyl, isopropyl, 2-butyl, 2-pentyl and 3-pentyl.

$C_{1-6}$-alkoxy is a straight-chain or branched alkoxy radical having 1 to 6, preferably 1 to 4, particularly preferably having 1 to 3 carbon atoms. Preferred examples include methoxy, ethoxy, n-propoxy, isopropoxy, tert-butoxy, n-pentoxy and n-hexoxy.

$C_1$-$C_6$-alkoxycarbonyl is a straight-chain or branched alkoxycarbonyl radical having 1 to 6, preferably 1 to 4 and particularly preferably 1 to 3 carbon atoms. Preferred examples include methoxycarbonyl, ethoxycarbonyl, n-propoxycarbonyl, isopropoxycarbonyl and tert-butoxycarbonyl.

$C_1$-$C_6$-alkylamino is a straight-chain or branched mono- or dialkylamino radical having 1 to 6, preferably 1 to 4 and particularly preferably having 1 to 3 carbon atoms. Preferred examples include methylamino, ethylamino, n-propylamino, isopropylamino, tert-butylamino, n-pentylamino and n-hexylamino, dimethylamino, diethylamino, di-n-propylamino, diisopropylamino, di-tert-butylamino, di-n-pentylamino, di-n-hexylamino, ethylmethylamino, isopropylmethylamino, n-butylethylamino and n-hexyl-i-pentylamino.

$C_1$-$C_6$-alkylaminocarbonyl is a mono- or dialkylamino radical which is linked via a carbonyl group, where the alkyl radicals may be identical or different, are straight-chain or branched and each comprise 1 to 6, preferably 1 to 4, and particularly preferably 1 to 3 carbon atoms. Preferred examples include methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, dimethylaminocarbonyl, diethylaminocarbonyl, di-n-propylaminocarbonyl, diisopropylaminocarbonyl, di-t-butylaminocarbonyl, di-n-pentylaminocarbonyl, di-n-hexylaminocarbonyl, ethylmethylaminocarbonyl, isopropylmethylaminocarbonyl, n-butylethylaminocarbonyl and n-hexyl-i-pentylaminocarbonyl. A further possibility in the case of a dialkylamino radical is for the two alkyl radicals to form together with the nitrogen atom to which they are bonded a 5- to 8-membered heterocyclyl.

$C_1$-$C_6$-alkylcarbonyl is a straight-chain or branched alkylcarbonyl radical having 1 to 6 and preferably 1 to 4 carbon atoms. Examples which may be mentioned are: acetyl, ethylcarbonyl, propylcarbonyl, isopropylcarbonyl, butylcarbonyl, isobutylcarbonyl, pentylcarbonyl and hexylcarbonyl. Acetyl and ethylcarbonyl are particularly preferred.

$C_1$-$C_6$-alkylsulfonyl is a straight-chain or branched alkylsulfonyl radical having 1 to 6, preferably 1 to 4 and particularly preferably having 1 to 3 carbon atoms. Preferred examples include methylsulfonyl, ethylsulfonyl, n-propylsulfonyl, isopropylsulfonyl, tert-butylsulfonyl, n-pentylsulfonyl and n-hexylsulfonyl.

$C_1$-$C_6$-alkylthio is a straight-chain or branched alkylthio radical having 1 to 6, preferably 1 to 4 and particularly preferably having 1 to 3 carbon atoms. Preferred examples include methylthio, ethylthio, n-propylthio, isopropylthio, tert-butylthio, n-pentylthio and n-hexylthio.

Halogen is fluorine, chlorine, bromine and iodine. Fluorine, chlorine, bromine are preferred, and fluorine and chlorine are particularly preferred.

Heteroaryl is an aromatic, monocyclic radical having 5 to 6 ring atoms and up to 3 hetero atoms from the series S, O and/or N. 5- to 6-Membered heteroaryls having up 2 hetero atoms are preferred. The heteroaryl radical may be bonded via a carbon or nitrogen atom. Preferred examples include thienyl, furyl, pyrrolyl, thiazolyl, oxazolyl, imidazolyl, tetrazolyl, pyridyl, pyrimidinyl and pyridazinyl 3- to 8-membered cycloalkyl is saturated and partially unsaturated nonaromatic cyclo-alkyl radicals having 3 to 8, preferably 3 to 6 and particularly preferably 5 to 6 carbon atoms in the ring. Preferred examples include cyclopropyl, cyclobutyl, cyclopentyl, cyclopentenyl, cyclohexyl and cyclohexenyl.

5- to 8-membered heterocyclyl is a mono- or polycyclic, heterocyclic radical having 5 to 8 ring atoms and up to 3, preferably 2, hetero atoms or hetero groups from the series N, O, S, SO, $SO_2$. Mono- or bicyclic heterocyclyl is preferred. Monocyclic heterocyclyl is particularly preferred. N and O are preferred as hetero atoms. The heterocyclyl radicals may be saturated or partially unsaturated. Saturated heterocyclyl radicals are preferred. 5- to 7-Membered heterocyclyl radicals are particularly preferred. Preferred examples include oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl.

When radicals in the compounds of the invention are optionally substituted, unless otherwise specified substitution by up to three identical or different substituents is preferred.

A further embodiment of the invention relates to compounds of the formula (I)

in which
A is $C_1$-$C_5$-alkyl or $C_3$-$C_6$-cycloalkyl, which are optionally substituted by up to 3 radicals independently of one another selected from the group of $C_1$-$C_4$-alkyl, $C_1$-$C_4$-alkoxy, hydroxycarbonyl, cyano, amino, hydroxy, $C_1$-$C_4$-alkylamino, fluorine, chlorine, bromine, $C_1$-$C_4$-alkoxycarbonyl, $C_1$-$C_6$-alkylcarbonyl, $C_1$-$C_4$-alkylsulfonyl and $C_1$-$C_4$-alkylthio,
where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$,
where
$R^3$ and $R^4$ are independently of one another hydrogen or $C_1$-$C_4$-alkyl,
or
$R^3$ and $R^4$ together with the nitrogen atom to which they are bonded are 5- to 6-membered heterocyclyl,
B is phenyl, thienyl or pyridyl, which are optionally substituted by up to 3 radicals in each case independently of one another selected from the group of $C_1$-$C_4$-alkyl, $C_1$-$C_4$-alkoxy, hydroxycarbonyl, cyano, trifluoromethyl, trifluoromethoxy, amino, hydroxy, $C_1$-$C_4$-alkylamino, fluorine, chlorine, bromine, $C_1$-$C_4$-alkylaminocarbonyl, $C_1$-$C_4$-alkoxycarbonyl, $C_1$-$C_4$-alkylcarbonyl, $C_1$-$C_4$-alkylsulfonyl and $C_1$-$C_4$-alkylthio,
where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$,
where
$R^3$ and $R^4$ have the abovementioned meanings, and the salts, solvates and/or solvates of the salts thereof.

A further embodiment of the invention relates to compounds of the formula (I)

in which
A has the abovementioned meanings, and
B is phenyl or pyridyl which are optionally substituted by up to 3 radicals in each case independently of one another selected from the group of methyl, ethyl, 2-propyl, trifluoromethyl, methoxy, ethoxy, fluorine and chlorine,
where one of the radicals on the phenyl or pyridyl is located in the ortho position relative to the attachment point of the amino function, and the salts, solvates and/or solvates of the salts thereof.

A further embodiment of the invention relates to compounds of the formula (I)

in which
A is $C_3$-$C_6$-cycloalkyl, and
B has the abovementioned meanings, and the salts, solvates and/or solvates of the salts thereof.

A further embodiment of the invention relates to compounds of the formula (I)

in which
A is 2-methylpropyl, 2-butyl, 2-pentyl or 3-pentyl, and
B has the abovementioned meanings, and the salts, solvates and/or solvates of the salts thereof.

A further embodiment of the invention relates to compounds of the formula (I)

in which
A is $C_3$-$C_5$-alkyl or $C_5$-$C_6$-cycloalkyl,
B is phenyl, thienyl or pyridyl, which are optionally substituted by up to 3 radicals in each case independently of one another selected from the group of $C_1$-$C_3$-alkyl, trifluoromethyl, hydroxy, methoxy, ethoxy, cyano, dimethylamino, diethylamino, methoxycarbonyl, ethoxycarbonyl, methylcarbonyl, ethylcarbonyl, fluorine and chlorine, and the salts, solvates and/or solvates of the salts thereof.

A process for preparing the compounds of the invention of the formula (I) has additionally been found, characterized in that a compound of the formula

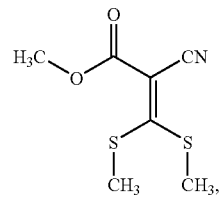

(II)

is initially converted with a compound of the formula $H_2N$—B (III)

in which
B has the abovementioned meanings, at elevated temperature in an inert solvent or else in the absence of a solvent into a compound of the formula

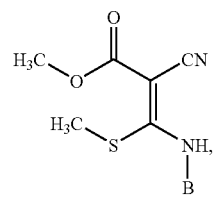

(IV)

in which
B has the abovementioned meanings, and the latter is then reacted in an inert solvent in the presence of a base with a compound of the formula

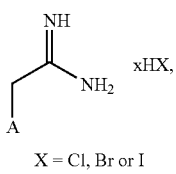

X = Cl, Br or I in which
A has the abovementioned meanings, and the resulting compounds of the formula (I) are reacted where appropriate with the appropriate (i) solvents and/or (ii) bases or acids to give their solvates, salts and/or solvates of the salts.

The compound of the formula (II) is known from the literature (R. Gompper, W. Toepfl, Chem. Ber. 1962, 95, 2861-2870). The compounds of the formulae (III) and (V) are commercially available, known from the literature or can be prepared in analogy to processes known from the literature (see, for example, H. Gielen, C. Alonso-Alija, M. Hendrix, U. Niewöhner, D. Schauss, Tetrahedron Lett. 2002, 43, 419-421).

Solvents suitable for process step (II)+(III)→(IV) are high-boiling, inert organic solvents which are not changed under the reaction conditions. These preferably include dimethylformamide, dimethyl sulfoxide or sulfolane. It is likewise possible to carry out the reaction without solvent in the melt. The reaction is particularly preferably carried out without solvent or in dimethylformamide.

The reaction generally takes place in a temperature range from +100° C. to +200° C., preferably in a temperature range from +125° C. to +150° C. The reaction can be carried out under atmospheric, elevated or reduced pressure (e.g. from 0.5 to 5 bar). It is generally carried out under atmospheric pressure.

The compound of the formula (III) is in this case employed in an amount of from 1 to 2 mol, preferably in an equivalent amount of 1 mol, based on 1 mol of the compound of the formula (II).

Solvents suitable for process step (IV)+(V)→(I) are the usual organic solvents which are not changed under the reaction conditions. These preferably include dimethylformamide, dimethyl sulfoxide, acetonitrile, dioxane or alcohols such as methanol, ethanol, propanol, isopropanol, n-butanol or tert-butanol. It is likewise possible to employ mixtures of the solvents mentioned. Dimethylformamide or acetonitrile is particularly preferred.

The reaction generally takes place in a temperature range from +50° C. to +150° C., preferably in a temperature range from +70° C. to +100° C. The reaction can be carried out under atmospheric, elevated or reduced pressure (e.g. from 0.5 to 5 bar). It is generally carried out under atmospheric pressure.

Bases suitable for process step (IV)+(V)→(I) are preferably alkali metal carbonates such as lithium, sodium, potassium or cesium carbonate or organic amine bases such as, for example, pyridine, triethylamine, ethyldiisopropylamine, N-methylmorpholine or N-methylpiperidine. Potassium carbonate is particularly preferred.

The base is in this case employed in an amount of from 1.5 to 4 mol, preferably in an amount of from 1.5 to 2 mol, based on 1 mol of the compound of the formula (IV). The compound of the formula (V) is employed in an amount of from 1 to 1.5 mol, preferably in an amount of 1.2 mol, based on 1 mol of the compound of the formula (IV).

The process of the invention can be illustrated for example by the following formula diagram:

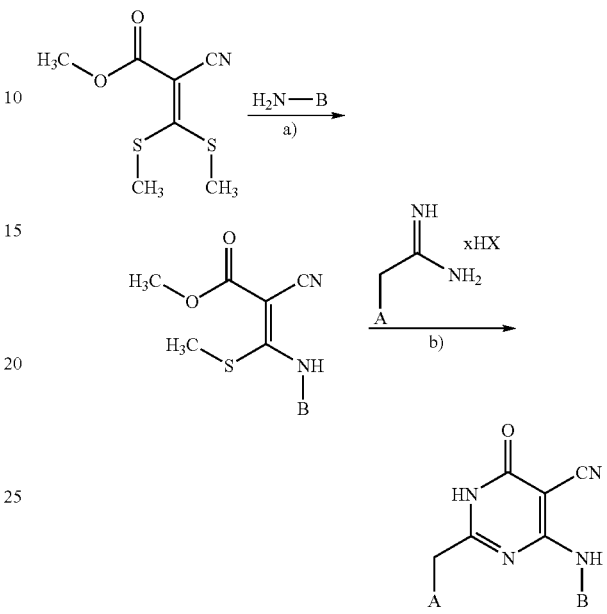

a) 150° C., 2 h; b) potassium carbonate, DMF, 90° C., 16 h.

The compounds of the invention show a valuable range of pharmacological effects which could not have been predicted. They are distinguished in particular by inhibition of PDE9A.

It has surprisingly been found that the compounds of the invention are suitable for producing medicaments for improving perception, concentration, learning or memory.

The compounds of the invention can, by reason of their pharmacological properties, be employed alone or in combination with other medicaments for improving perception, concentration, learning and/or memory.

The compounds of the invention are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

The in vitro effect of the compounds of the invention can be shown with the following biological assays:

PDE Inhibition

Recombinant PDE1C (GenBank/EMBL Accession Number: NM_005020, Loughney et al. J. Biol. Chem. 1996 271, 796-806), PDE2A (GenBank/EMBL Accession Number:

NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene*. 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472-476), PDE8A (GenBank/EMBL Accession Number: AF_056490, Fisher et al. *Biochem. Biophys. Res. Commun.* 1998, 246, 570-577), PDE9A (Fisher et al., *J. Biol. Chem*, 1998, 273 (25): 15559-15564), PDE10A (GenBank/EMBL Accession Number: NM_06661, Fujishige et al. J Biol Chem. 1999, 274, 18438-45), PDE11A (GenBank/EMBL Accession Number: NM_016953, Fawcett et al. *Proc. Natl. Acad. Sci*. 2000, 97, 3702-3707) were expressed in Sf9 cells with the aid of the pFASTBAC baculovirus expression system (GibcoBRL).

The test substances are dissolved in 100% DMSO and serially diluted to determine their in vitro effect on PDE 9A. Typically, serial dilutions from 200 µM to 1.6 µM are prepared (resulting final concentrations in the assay: 4 µM to 0.032 µM). 2 µL portions of the diluted substance solutions are introduced into the wells of microtiter plates (Isoplate; Wallac Inc., Atlanta, Ga.). Then 50 µL of a dilution of the PDE9A preparation described above are added. The dilution of the PDE9A preparation is chosen so that less than 70% of the substrate is converted during the subsequent incubation (typical dilution: 1:10 000; dilution buffer: 50 mM Tris/HCl pH 7.5, 8.3 mM $MgCl_2$, 1.7 mM EDTA, 0.2% BSA). The substrate, [8-$^3$H] guanosine 3',5'-cyclic phosphate (1 µCi/µL; Amersham Pharmacia Biotech., Piscataway, N.J.) is diluted 1:2000 with assay buffer (50 mM Tris/HCl pH 7.5, 8.3 mM $MgCl_2$, 1.7 mM EDTA) to a concentration of 0.0005 µCi/µL. The enzyme reaction is finally started by adding 50 µL (0.025 µCi) of the diluted substrate. The assay mixtures are incubated at room temperature for 60 min and the reaction is stopped by adding 25 µl of a PDE9A inhibitor (e.g. the inhibitor from preparation example 1, final concentration 10 µM) dissolved in assay buffer. Immediately thereafter, 25 µL of a suspension containing 18 mg/mL Yttrium Scintillation Proximity Beads (Amersham Pharmacia Biotech., Piscataway, N.J.) are added. The microtiter plates are sealed with a film and left to stand at room temperature for 60 min. The plates are then measured for 30 s per well in a Microbeta scintillation counter (Wallac Inc., Atlanta, Ga.). $IC_{50}$ values are determined from the graphical plot of the substance concentration versus the percentage inhibition.

Representative examples of the PDE9A-inhibiting effect of the compounds of the invention are listed in Tables 1 and 2 on the basis of the $IC_{50}$ values:

TABLE 1

Inhibition of PDE isoenzymes by Example 3

| Isoenzyme | Species | $IC_{50}$ [nM] |
|---|---|---|
| PDE1C | human | >4000 |
| PDE2A | human | >4000 |
| PDE3B | human | >4000 |
| PDE4B | human | >4000 |
| PDE5A | human | 1400 |
| PDE7A | human | >4000 |
| PDE8A | human | >4000 |
| PDE9A | human | 52 |
| PDE10A | human | >4000 |

TABLE 2

PDE9A-inhibiting effect of compounds of the invention

| Example | $IC_{50}$ [nM] |
|---|---|
| 1 | 75 |
| 3 | 52 |
| 7 | 54 |
| 14 | 75 |
| 23 | 87 |

The in vitro effect of test substances on recombinant PDE3B, PDE4B, PDE7B, PDE8A, PDE10A and PDE11A is determined in accordance with the assay protocol described above for PDE 9A with the following adaptations: [5',8-$^3$H] adenosine 3',5'-cyclic phosphate (1 µCi/µL; Amersham Pharmacia Biotech., Piscataway, N.J.) is used as substrate. Addition of an inhibitor solution to stop the reaction is unnecessary. Instead, the incubation of substrate and PDE is followed immediately by addition of the yttrium scintillation proximity beads as described above and thus the reaction is stopped. To determine a corresponding effect on recombinant PDE1C, PDE2A and PDE5A, the protocol is additionally adapted as follows: with PDE1C, additionally $10^{-7}$ M calmodulin and 3 mM $CaCl_2$ are added to the reaction mixture. PDE2A is stimulated in the assay by adding 1 µM cGMP and is assayed with a BSA concentration of 0.01%. The substrate employed for PDE1C and PDE2A is [5',8-$^3$H] adenosine 3',5'-cyclic phosphate (1 µCi/µL; Amersham Pharmacia Biotech., Piscataway, N.J.), and for PDE5A is [8-$^3$H] guanosine 3',5'-cyclic phosphate (1 µCi/µL; Amersham Pharmacia Biotech., Piscataway, N.J.).

Long-Term Potentiation

Long-term potentiation is regarded as a cellular correlate of learning and memory processes. The following method can be used to determine whether PDE 9 inhibition has an influence on long-term potentiation:

Rat hippocampi are placed at an angle of about 70 degrees to the cutting blade (chopper). 400 µm-thick slices of the hippocampus are prepared. The slices are removed from the blade using a very soft, thoroughly wetted brush (marten hair) and transferred into a glass vessel with cold nutrient solution (124 mM NaCl, 4.9 mM KCl, 1.3 mM $MgSO_4 \times 7\ H_2O$, 2.5 mM $CaCl_2^{2+}$ anhydrous, 1.2 mM $KH_2PO_4$, 25.6 mM $NaHCO_3$, 10 mM glucose, pH 7.4) gassed with 95% $O_2$/5% $CO_2$. During the measurement, the slices are kept in a temperature-controlled chamber under a 1-3 mm-high liquid level. The flow rate is 2.5 mil/min. The preliminary gassing takes place under a slightly elevated pressure (about 1 atm) and through a microneedle in the prechamber. The slice chamber is connected to the prechamber in such a way that a minicirculation can be maintained. The minicirculation is driven by the 95% $O_2$/5% $CO_2$ flowing out through the microneedle. The freshly prepared hippocampus slices are adapted in the slice chamber at 33° C. for at least 1 hour.

The stimulus level is chosen so that the focal excitatory postsynaptic potentials (fEPSP) are 30% of the maximum excitatory postsynaptic potential (EPSP). A monopolar stimulation electrode consisting of lacquered stainless steel, and a constant-current biphasic stimulus generator (AM Systems 2100) are used for local stimulation of the Schaffer collaterals (voltage: 1-5 V, pulse width of one polarity 0.1 ms, total pulse 0.2 ms). Glass electrodes (borosilicate glass with filament, 1-5 MOhm, diameter: 1.5 mm, tip diameter: 3-20 µm), filled with normal nutrient solution, are used to record the excitatory postsynaptic potentials (fEPSP) from the stratum radiatum. The field potentials are measured versus a chlorinated silver reference electrode located at the edge of the slice chamber using a DC voltage amplifier. The field potentials are filtered through a low-pass filter (5 kHz). The slope of the fEPSPs (fEPSP slope) is determined for the statistical analysis of the experiments. The recording, analysis and control of the experiment takes place with the aid of a software program (PWIN) which was developed in the Department of Neurophysiology. The formation of the average fEPSP slopes at the respective time points and construction of the diagrams takes place with the aid of the EXCEL software, with automatic data recording by an appropriate macro.

Superfusion of the hippocampus slices with a 10 μM solution of the compounds of the invention leads to a significant increase in the LTP.

The in vivo effect of the compounds of the invention can be shown for example as follows:

Social Recognition Test

The social recognition test is a learning and memory test. It measures the ability of rats to distinguish between known and unknown members of the same species. This test is therefore suitable for examining the learning- or memory-improving effect of the compounds of the invention.

Adult rats housed in groups are placed singly in test cages 30 min before the start of the test. Four min before the start of the test, the test animal is put in an observation box. After this adaptation time, a juvenile animal is put in with the test animal and the absolute time for which the adult animal inspects the young one is measured for 2 min (trial 1). All behaviors clearly directed at the young animal are measured, i.e. anogenital inspection, pursuit and grooming, during which the old animal was no further than 1 cm from the young animal. The juvenile is then removed, and the adult is treated with a compound of the invention or vehicle and subsequently returned to its own cage. The test is repeated after a retention time of 24 hours (trial 2). A diminished social interaction time compared with trial 1 indicates that the adult rat remembers the young animal.

The adult animals receive intraperitoneal injections either within a defined time period (e.g. one hour) before trial 1 or directly following trial 1 either with vehicle (10% ethanol, 20% Solutol, 70% physiological saline) or 0.1 mg/kg, 0.3 mg/kg, 1.0 mg/kg or 3.0 mg/kg compound of the invention dissolved in 10% ethanol, 20% Solutol, 70% physiological saline. Vehicle-treated rats show no reduction in the social interaction time in trial 2 compared with trial 1. They have consequently forgotten that they have already had contact with the young animal. Surprisingly, the social interaction time in the second run after treatment with the compounds of the invention is significantly reduced compared with those treated with vehicle. This means that the substance-treated rats have remembered the juvenile animal and thus the compounds of the invention display an improving effect on learning and memory.

The novel active ingredients can be converted in a known manner into conventional formulations such as tablets, coated tablets, pills, granules, aerosols, syrups, emulsions, suspensions and solutions, by use of inert, nontoxic, pharmaceutically suitable carriers or solvents. In these cases, the therapeutically effective compound is to be present in each case in a concentration of about 0.5 to 90% by weight in the complete mixture, i.e. in amounts which are sufficient to achieve the indicated dosage range.

The formulations can be produced for example by diluting the active ingredients with solvents and/or carriers, where appropriate with use of emulsifiers and/or dispersants, it being possible for example in the case where water is used as diluent where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved to be advantageous to administer amounts of about 0.001 to 10, on oral administration preferably about 0.005 to 3, mg/kg of body weight to achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, whereas in other cases the stated upper limit must be exceeded. If larger amounts are administered, it may be advisable to divide these into a plurality of single doses over the day.

Unless indicated otherwise, all stated amounts refer to percentages by weight. Solvent ratios, dilution ratios and concentrations stated for liquid/liquid solutions are based in each case on volume. The statement "w/v" means "weight/volume". Thus, for example, "10% w/v" means 100 ml of solution or suspension contain 10 g of substance.

Abbreviations:

| | |
|---|---|
| DMF | N,N-dimethylformamide |
| DMSO | dimethylsulfoxide |
| ESI | electrospray ionization (in MS) |
| h | hour (s) |
| HPLC | high pressure, high performance liquid chromatography |
| LC-MS | coupled liquid chromatography-mass spectroscopy |
| min | minutes |
| MS | mass spectroscopy |
| NMR | nuclear magnetic resonance spectroscopy |
| RT | room temperature |
| $R_t$ | retention time (in HPLC) |
| THF | tetrahydrofuran |

HPLC and LC-MS Methods:

Method 1:

Instrument: Micromass Quattro LCZ, with HPLC Agilent series 1100; column: Grom-Sil 120 ODS-4 HE, 50 mm×2.0 mm, 3 μm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 2:

MS instrument type: Micromass ZQ; HPLC instrument type: Waters Alliance 2795; column: Phenomenex Synergi 2 μp Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 3:

MS instrument type: Micromass ZQ; HPLC instrument type: HP 1100 series, UV DAD; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 0% B→2.9 min 70% B→3.1 min 90% →4.5 min 90% B; oven: 50° C.; flow rate: 0.8 ml/min; UV detection: 210 nm.

Method 4:

MS instrument type: Micromass ZQ; HPLC instrument type: Waters Alliance 2795; column: Merck Chromolith SpeedROD RP-18e 50 mm×4.6 mm; eluent A: water+500 µl of 50% strength formic acid/l, eluent B: acetonitrile+500 µl of 50% formic acid/l, gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 5:

MS instrument type: Micromass ZQ; HPLC instrument type: HP 1100 series; UV DAD; column: Phenomenex Synergi 2 µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 6:

Instrument: Micromass Quattro LCZ with HPLC Agilent series 1100; column: Phenomex Synergi 2 µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 208-400 nm.

Method 7:

MS instrument type: Micromass ZQ; HPLC instrument type: Waters Alliance 2790; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 8:

Instrument: HP 1100 with DAD detection; column: Kromasil RP-18, 60 mm×2 mm, 3.5 µm; eluent A: 5 ml of HclO$_4$/H$_2$O, eluent B: acetonitrile; gradient: 0 min 2% B→0.5 min 2% B→4.5 min 90% B→6.5 min 90% B; flow rate: 0.75 ml/min; temperature: 30° C.; UV detection 210 nm.

Method 9:

Instrument: Micromass Platform LCZ with HPLC Agilent series 1100; column: Phenomenex Synergi 2 µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A flow rate 1 ml/min→2.5 min 30% A flow rate 2 ml/min→3.0 min 5% A flow rate 2 ml/min→4.5 min 5% A flow rate 2 ml/min; oven: 50° C.; UV detection: 210 nm.

Method 10:

MS instrument type: Micromass ZQ; HPLC instrument type: Waters Alliance 2790; column: Grom-Sil 120 ODS-4 HE 50 mm×2 mm, 3.0 µm; eluent A: water+500 µl of 50% formic acid/l, eluent B: acetonitrile+500 µl of 50% formic acid/l; gradient: 0.0 min 0% B→0.2 min 0% B→2.9 min 70% B→3.1 min 90% B→4.5 min 90% B; oven: 45° C.; flow rate: 0.8 ml/min; UV detection: 210 nm.

Starting compounds:

EXAMPLE 1A

2-Cyclopentylethanamidine hydrochloride

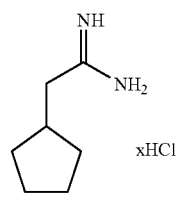

In an argon atmosphere, 58.2 g (1.09 mol) of ammonium chloride are suspended in 350 ml of toluene and cooled to 0° C. 544 ml of a 2M solution of trimethylaluminum in toluene are added dropwise, and the mixture is then stirred at RT for 2h. 34 g (217 mmol) of ethyl cylopentylacetate are then added. The mixture is then stirred at 80° C. overnight. After cooling to 0° C., 400 ml of methanol are added dropwise, and then the resulting solid is filtered off with suction. It is thoroughly washed with methanol several times, and the combined filtrates are concentrated in vacuo. The residue is suspended in dichloromethane/methanol 10:1 and the insoluble solid is again removed. The filtrate then obtained is concentrated and affords 23 g (65% of theory) of the desired product.

MS (ESIpos): m/z=127 [M+H]$^+$ (free base).

2-Cyclohexylethanamidine hydrochloride and 3-methylpentanamidine hydrochloride are prepared in analogy to Example 1A from the respective esters in a yield of 56% and 61% respectively (see also H. Gielen, C. Alonso-Alija, M. Hendrix, U. Niewöhner, D. Schauss, *Tetrahedron Lett.*, 2002, 43, 419-421).

EXAMPLE 2A

Methyl 2-cyano-3-[(4-fluorophenyl)amino]-3-(methylsulfanyl)-2-propenoate

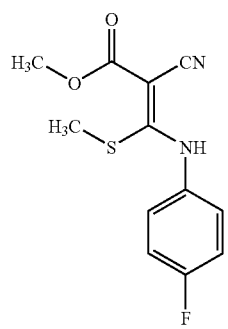

0.5 g (4.5 mmol) of 4-fluoroaniline is thoroughly mixed with 0.91 g (4.5 mmol) of methyl 3,3-bis(methylthio)-2-cyanoacrylate (R. Gompper, W. Toepfl, *Chem. Ber.* 1962, 95, 2861-2870). The reaction mixture is heated at 150° C. for 2 h, resulting in a melt. After cooling, a pale solid is obtained and is washed several times with methanol. 0.68 g (55.7% of theory) of the desired product is obtained.

LC-MS (method 1): $R_t$=2.6 min.
MS (ESIpos): m/z=267 [M+H]$^+$.

EXAMPLE 3A

Methyl 2-cyano-3-[(4-methyl-3-pyridinyl)amino]-3-(methylsulfanyl)-2-propenoate

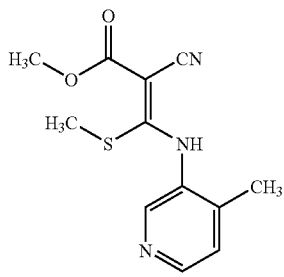

In analogy to the preparation of Example 2A, 1.4 g (29.6% of theory) of the title compound are obtained as a solid from 2.0 g (18.49 mmol) of 3-amino-4-methylpyridine and 3.76 g (18.49 mmol) of methyl 3,3-bis(methylthio)-2-cyanoacrylate.

EXAMPLE 4A

Methyl 2-cyano-3-[(3-fluorophenyl)amino]-3-(methylsulfanyl)-2-propenoate

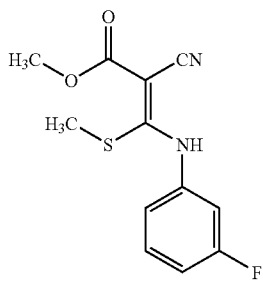

In analogy to the preparation of Example 2A, 0.43 g (36% of theory) of the title compound is obtained as a solid from 0.5 g (4.5 mmol) of 3-fluoroaniline and 0.91 g (4.5 mmol) of methyl 3,3-bis(methylthio)-2-cyanoacrylate.
LC-MS (method 1): $R_t$=2.63 min.
MS (ESIpos): m/z=267 [M+H]$^+$.

EXAMPLE 5A

Methyl 2-cyano-3-[(3-chlorophenyl)amino]-3-(methylsulfanyl)-2-propenoate

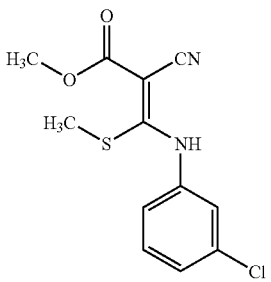

In analogy to the preparation of Example 2A, 0.53 g (48% of theory) of the title compound is obtained as a solid from 0.5 g (3.9 mmol) of 3-chloroaniline and 0.79 g (3.9 mmol) of methyl 3,3-bis(methylthio)-2-cyanoacrylate.

LC-MS (method 1): $R_t$=2.78 min.

MS (ESIpos): m/z=283 [M+H]$^+$.

EXAMPLE 6A

Methyl 2-cyano-3-[(3-methoxyphenyl)amino]-3-(methylsulfanyl)-2-propenoate

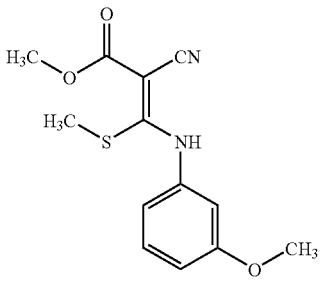

In analogy to the preparation of Example 2A, 0.47 g (41% of theory) of the title compound is obtained as a solid from 0.5 g (4.0 mmol) of 3-methoxyaniline and 0.8 g (4.0 mmol) of methyl 3,3-bis(methylthio)-2-cyanoacrylate.

LC-MS (method 1): $R_t$=2.63 min.

MS (ESIpos): m/z=279 [M+H]$^+$.

EXAMPLE 7A

Methyl 2-cyano-3-[(3-fluoro-2-methylphenyl)amino]-3-(methylsulfanyl)-2-propenoate

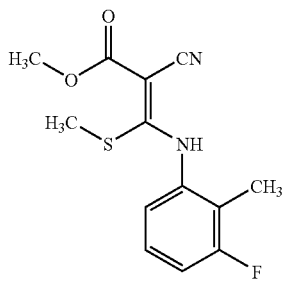

In analogy to the preparation of Example 2A, 0.15 g (34% of theory) of the title compound is obtained as a solid from 0.2 g (1.59 mmol) of 3-fluoro-2-methylaniline and 0.32 g (1.59 mmol) of methyl 3,3-bis(methylthio)-2-cyanoacrylate.
LC-MS (method 6): $R_t$=2.5 min.
MS (ESIpos): m/z=281 [M+H]$^+$.

EXAMPLE 8A

Methyl 2-cyano-3-[(2,5-dimethylphenyl)amino]-3-(methylsulfanyl)-2-propenoate

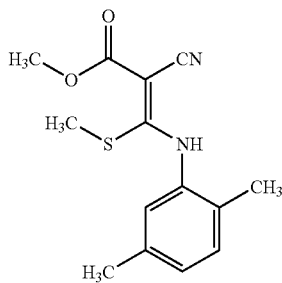

In analogy to the preparation of Example 2A, 0.9 g (75% of theory) of the title compound is obtained as a solid from 0.54 g (4.4 mmol) of 2,5-dimethylaniline and 0.9 g (4.4 mmol) of methyl 3,3-bis(methylthio)-2-cyanoacrylate.
LC-MS (method 1): $R_t$=2.91 min.
MS (ESIpos): m/z=277 [M+H]$^+$.

EXAMPLE 9A

Methyl 2-cyano-3-[(2-methoxyphenyl)amino]-3-(methylsulfanyl)-2-propenoate

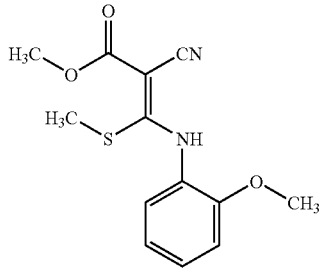

In analogy to the preparation of Example 2A, 0.9 g (67% of theory) of the title compound is obtained as a solid from 0.6 g (5.0 mmol) of 2-methoxyaniline and 1.0 g (5.0 mmol) of methyl 3,3-bis(methylthio)-2-cyanoacrylate.
LC-MS (method 7): $R_t$=3.01 min.
MS (ESIpos): m/z=279 [M+H]$^+$.
$^1$H-NMR (300 MHz, DMSO-d$_6$): δ=2.28 (s, 3H), 3.71 (s, 3H), 3.84 (s, 3H), 7.00 (m, 1H), 7.17 (m, 1H), 7.33 (m, 1H), 7.41 (m, 1H).

EXAMPLE 10A

Methyl 2-cyano-3-[(4-fluoro-2-methylphenyl)amino]-3-(methylsulfanyl)-2-propenoate

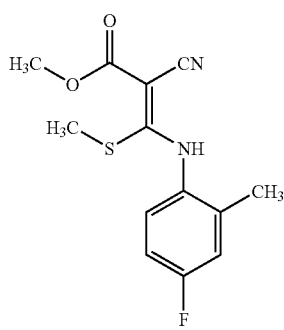

In analogy to the preparation of Example 2A, 0.7 g (50% of theory) of the title compound is obtained as a solid from 0.62 g (5.0 mmol) of 2-methyl-4-fluoroaniline and 1.01 g (5.0 mmol) of methyl 3,3-bis(methylthio)-2-cyanoacrylate.

LC-MS (method 4): $R_t$=2.28 min.
MS (ESIpos): m/z=281 [M+H]$^+$.
$^1$H-NMR (300 MHz, DMSO-d$_6$): δ=2.22 (s, 3H), 2.27 (s, 3H), 3.70 (s, 3H), 7.11 (m, 1H), 7.23 (m, 1H), 7.33 (m, 1H), 7.34 (m, 1H).

EXAMPLE 11A

Methyl 2-cyano-3-[(2-methylphenyl)amino]-3-(methylsulfanyl)-2-propenoate

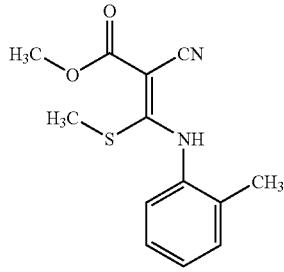

In analogy to the preparation of Example 2A, 2.5 g (63% of theory) of the title compound are obtained as a solid from 1.6 g (15.0 mmol) of 2-methylaniline and 3.01 g (15.0 mmol) of methyl 3,3-bis(methylthio)-2-cyanoacrylate.

LC-MS (method 7): $R_t$=3.08 min.

MS (ESIpos): m/z=263 [M+H]$^+$.

$^1$H-NMR (300 MHz, DMSO-d6): δ=2.27 (s, 3H), 2.23 (s, 3H), 3.70 (s, 3H), 7.28 (m, 4H).

EXAMPLE 12A

Methyl 2-cyano-3-(methylsulfanyl)-3-[(2-propylphenyl)amino]-2-propenoate

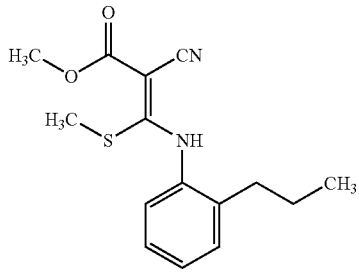

In analogy to the preparation of Example 2A, 0.7 g (61% of theory) of the title compound is obtained as a solid from 0.5 g (3.7 mmol) of 2-propylaniline and 0.7 g (3.7 mmol) of methyl 3,3-bis(methylthio)-2-cyanoacrylate.

LC-MS (method 3): $R_t$=3.52 min.

MS (ESIpos): m/z=291 [M+H]$^+$.

EXAMPLE 13A

Methyl 2-cyano-3-(methylsulfanyl)-3-(3-pyridinylamino)-2-propenoate

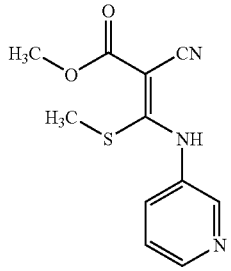

1.39 g (14.8 mmol) of 3-aminopyridine are dissolved in 50 ml of THF, cooled to −20° C., and 7.4 ml of a 2M solution of n-butyllithium in hexane are added. After stirring for 15 min, 2.00 g (9.84 mmol) of methyl 3,3-bis(methylthio)-2-cyanoacrylate are added. The mixture is warmed to room temperature while stirring and then hydrolyzed with ice-water. The product is extracted with dichloromethane. After drying over sodium sulfate, the solvent is removed in vacuo and the residue is purified by preparative HPLC. 0.44 g (18.1% of theory) of the desired product is obtained.

HPLC (method 8): $R_t$=3.06 min.

MS (ESIpos): m/z=250 [M+H]$^+$, 272 [M+Na]$^+$.

EXAMPLE 14A (3S)-3-Methylpentanenitrile

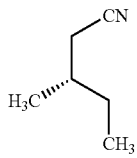

5 g (29.78 mmol) of (2S)-2-methylbutyl methanesulfonate are heated with 1.5 g (44.66 mmol) of sodium cyanide in 15 ml of dimethylformamide at 80° C. overnight. Cooling to room temperature is followed by dilution with 150 ml of water and extraction five times with diethyl ether. The combined organic phases are washed with water and with saturated sodium chloride solution. After drying over sodium sulfate, the solvent is removed in vacuo at room temperature. 2.3 g (67% of theory) of crude product are obtained and employed without further purification in the next stage.

$^1$H-NMR (200 MHz, DMSO-d$_6$): δ=0.87 (t, 3H), 0.92 (d, 3H), 1.30 (m, 2H), 1.67 (m, 1H), 2.42 (dd, 2H).

EXAMPLE 15A (3S)-3-Methylpentanamidine hydrochloride

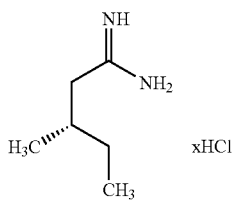

In an argon atmosphere, 1.1 g (20.5 mmol) of ammonium chloride are suspended in 20 ml of toluene and cooled to 0° C. 10.29 ml of a 2M solution of trimethylaluminum in toluene are added dropwise, and the mixture is then stirred at RT for 2 h. 1 g (10.29 mmol) of (3S)-3-methylpentanenitrile is then added. The mixture is then stirred at 80° C. overnight. After cooling to 0° C., 40 ml of methanol are added dropwise, and then the resulting solid is filtered off with suction. It is thoroughly washed with methanol several times, and the combined filtrates are concentrated in vacuo. The residue is suspended in dichloromethane/methanol 10:1 and the insoluble solid is again removed. The filtrate then obtained is concentrated and affords 1.01 g (64% of theory) of the desired product.

LC-MS (method 2): $R_t$=0.31 min.

MS (ESIpos): m/z=115 [M+H]$^+$(free base).

EXAMPLE 16A

Methyl 2-cyano-3-[(5-fluoro-2-methylphenyl)amino]-3-(methylsulfanyl)-2-propenoate

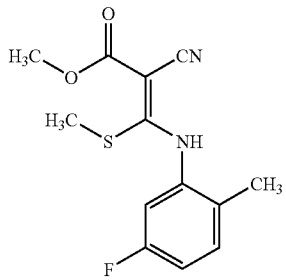

In analogy to the preparation of Example 2A, 1.7 g (52% of theory) of the title compound are obtained as a solid from 1.5 g (11.98 mmol) of 5-fluoro-2-methyl-aniline and 2.4 g (11.98 mmol) of methyl 3,3-bis(methylthio)-2-cyanoacrylate.

LC-MS (method 6): $R_t$=2.49 min.
MS (ESIpos): m/z=281 [M+H]$^+$.

Exemplary embodiments

EXAMPLE 1

2-(Cyclopentylmethyl)-4-[(fluorophenyl)amino]6-oxo-1,6-dihydro-5-pyrimidinecarbonitrile

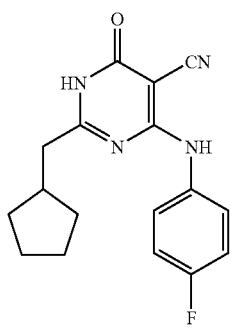

0.1 g (0.37 mmol) of methyl 2-cyano-3-[(4-fluorophenyl)amino]-3-(methylsulfanyl)-2-propenoate, 0.07 g (0.41 mmol) of 2-cyclopentylethanamidine hydrochloride and 0.11 g (0.82 mmol) of potassium carbonate are heated in 1 ml of dimethylformamide at 90° overnight. After filtration, the filtrate is acidified with concentrated hydro-chloric acid, whereupon the product precipitates. Washing with water several times and drying under high vacuum results in 54 mg (46% of theory) of the product as a colorless solid.

LC-MS (method 1): $R_t$=2.86 min.
MS (ESIpos): m/z=313 [M+H]$^+$.

$^1$H-NMR (300 MHz, DMSO-d$_6$): δ=1.13 (m, 2H), 1.56 (m, 6H), 2.15 (m, 1H), 2.44 (d, 2H), 7.15 (dd, 2H), 7.41 (dd, 2H), 9.66 (s, 1H), 12.36 (s, 1H).

EXAMPLE 2

2-(Cyclopentylmethyl)-4-[(4-methyl-3-pyridinyl)amino]-6-oxo-1,6-dihydro-5-pyrimidinecarbonitrile

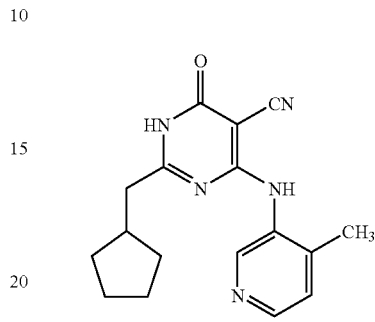

0.2 g (0.76 mmol) of methyl 2-cyano-3-[(4-methyl-3-pyridinyl)amino]-3-(methylsulfanyl)-2-propenoate are dissolved with 0.13 g (0.85 mmol) of 2-cyclopentylethanamidine hydrochloride and 0.23 g (1.67 mmol) of potassium carbonate in 4 ml of DMF and stirred at 90° C. for 3 days. After cooling, the product is purified by preparative HPLC (YMC Gel ODS-AQ S 5/15 μm; eluent A: water, eluent B: aceto-nitrile; gradient: 0 min 30% B, 5 min 30% B, 50 min 95% B) purified. 60 mg (25% of theory) of the product are obtained.

LC-MS (method 5): $R_t$=1.57 min.
MS (ESIpos): m/z=310 [M+H]$^+$.
$^1$H-NMR (300 MHz, DMSO-d$_6$): δ=1.04 (m, 2H), 1.51 (m, 6H), 2.01 (m, 1H), 2.28 (s, 3H), 2.39 (d, 2H), 7.51 (d, 1H), 8.41 (d, 1H), 8.52 (s, 1H), 12.41 (s, 1H).

EXAMPLE 3

2-(Cyclohexylmethyl)-4-[(4-methyl-3-pyridinyl)amino]-6-oxo-1,6-dihydro-5-pyrimidinecarbonitrile

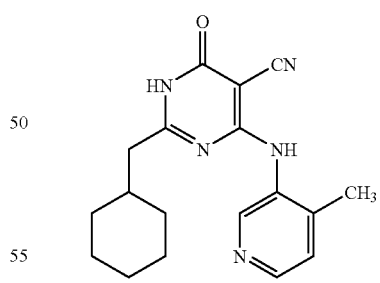

0.4 g (1.51 mmol) of methyl 2-cyano-3-[(4-methyl-3-pyridinyl)amino]-3-(methylsulfanyl)-2-propenoate are dissolved with 0.29 g (1.67 mmol) of 2-cyclohexylethanamidine hydrochloride and 0.46 g (3.3 mmol) of potassium carbonate in 5 ml of DMF and heated at 90° C. for 7 days. After cooling and filtration, the product is purified by preparative HPLC (YMC Gel ODS-AQ S 5/15 μm; eluent A; water, eluent B: acetonitrile, gradient: 0 min 30% B, 5 min 30% B, 50 min 95% B) purified. 433 mg (88% of theory) of the product are obtained.

LC-MS (method 5): $R_t$=1.47 min.

MS (ESIpos): m/z=324 [M+H]$^+$.

$^1$H-NMR (300 MHz, DMSO-d$_6$): δ=0.88 (m, 2H), 1.09 (m, 3H), 1.56 (m, 6H), 2.28 (d, 2H), 2.32 (s, 3H), 7.68 (s, 1H), 8.53 (d, 1H), 8.61 (s, 1H); 9.79 (s, 1H).

EXAMPLE 4

2-(Cyclopentylmethyl)-4-[(3-fluorophenyl)amino]-6-oxo-1,6-dihydro-5-pyrimidinecarbonitrile

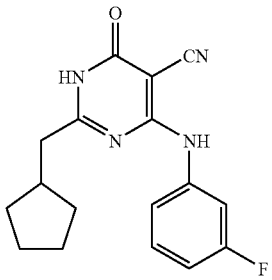

0.1 g (0.37 mmol) of methyl 2-cyano-3-[(3-fluorophenyl)amino]-3-(methylsulfanyl)-2-propenoate and 0.06 g (0.41 mmol) of 2-cyclopentylethanamidine hydrochloride are dissolved in 1 ml of DMF and heated with 0.11 g (0.82 mmol) of potassium carbonate at 90° C. overnight. After filtration, the solvent is removed in vacuo and the residue is purified by preparative HPLC (YMC Gel ODS-AQ S 5/15 μm; eluent A: water, eluent B: acetonitrile; gradient: 0 min 30% B, 5 min 30% B, 50 min 95% B) purified. 70 mg (59% of theory) of the product are obtained as a colorless solid.

LC-MS (method 1): $R_t$=2.9 min.

MS (ESIpos): m/z=313 [M+H]$^+$.

$^1$H-NMR (300 MHz, DMSO-d$_6$): δ=1.16 (m, 2H), 1.53 (m, 4H), 1.71 (m, 2H), 2.21 (m, 1H), 2.46 (d, 2H), 6.88 (m, 1H), 7.31 (m, 2H), 7.44 (m, 1H).

EXAMPLE 5

4-[(3-Chlorophenyl)amino]-2-(cyclopentylmethyl)-6-oxo-1,6-dihydro-5-pyrimidinecarbonitrile

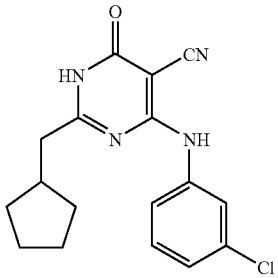

In analogy to the preparation of Example 4, 45 mg (39% of theory) of the title compound are obtained as a colorless solid from 0. g (0.35 mmol) of methyl 2-cyano-3-[(3-chlorophenyl)amino]-3-(methylsulfanyl)-2-propenoate, 0.06 g (0.38 mmol) of 2-cyclopentylethanamidine hydrochloride and 0.1 g (0.79 mmol) of potassium carbonate.

LC-MS (method 1): $R_t$=3.06 min.

MS (ESIpos): m/z=329 [M+H]$^+$ $^1$H-NMR (300 MHz, DMSO-d6): δ=1.14 (m, 2H), 1.55 (m, 4H), 1.71 (m, 2H), 2.19 (m, 1H), 2.46 (d, 2H), 7.19 (m, 1H), 7.38 (m, 2H), 7.63 (m, 1H), 9.78 (br. S, 1H), 12.49 (br. S, 1H).

EXAMPLE 6

2-(Cyclopentylmethyl)-4-[(3-methoxyphenyl)amino]-6-oxo-1,6-dihydro-5-pyrimidinecarbonitrile

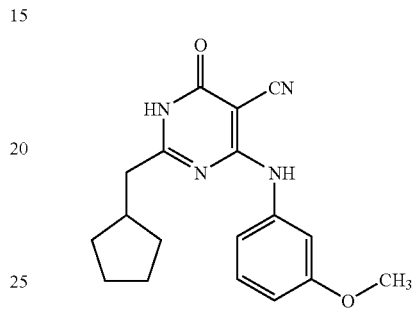

In analogy to the preparation of Example 4, 40 mg (42% of theory) of the title compound are obtained as a colorless solid from 0.08 g (0.28 mmol) of methyl 2-cyano-3-[(3-methoxyphenyl)amino]-3-(methylsulfanyl)-2-propenoate, 0.05 g (0.31 mmol) of 2-cyclopentylethanamidine hydrochloride and 0.09 g (0.63 mmol) of potassium carbonate.

LC-MS (method 1): $R_t$=2.84 min.

MS (ESIpos): m/z=325 [M+H]$^+$.

EXAMPLE 7

2-(Cyclopentylmethyl)-4-[(3-fluoro-2-methylphenyl)amino]-6-oxo-1,6-dihydro-5-pyrimidinecarbonitrile

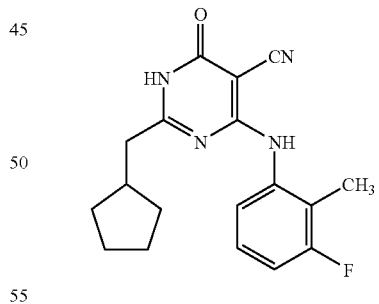

In analogy to the preparation of Example 4, 31 mg (35% of theory) of the title compound are obtained as a colorless solid from 0.075 g (0.27 mmol) of methyl 2-cyano-3-[(3-fluoro-2-methylphenyl)amino]-3-(methylsulfanyl)-2-propenoate, 0.047 g (0.29 mmol) of 2-cyclopentylethanamidine hydrochloride and 0.081 g (0.59 mmol) of potassium carbonate.

LC-MS (method 6): $R_t$=2.37 min.

MS (ESIpos): m/z=327 [M+H]$^+$.

$^1$H-NMR (300 MHz, DMSO-d$_6$): δ=1.08 (m, 2H), 1.43 (m, 4H), 1.55 (m, 2H), 2.04 (m, 1H), 2.04 (s, 3H), 2.39 (d, 2H), 7.05 (m, 2H), 7.20 (m, 1H), 9.60 (s, 1H), 12.30 (s, 1H).

EXAMPLE 8

2-(Cyclopentylmethyl)-4-[(2,5-dimethylphenyl)amino]-6-oxo-1,6-dihydro-5-pyrimidinecarbonitrile

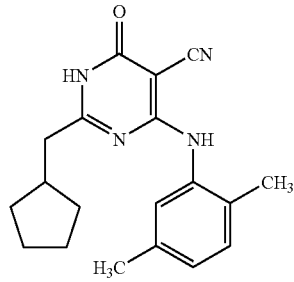

In analogy to the preparation of Example 4, 53 mg (45% of theory) of the title compound are obtained as a colorless solid from 0.1 g (0.37 mmol) of methyl 2-cyano-3-[(2,5-dimethylphenyl)amino]-3-(methylsulfanyl)-2-propenoate, 0.06 g (0.39 mmol) of 2-cyclopentylethanamidine hydrochloride and 0.1 g (0.79 mmol) of potassium carbonate.

LC-MS (method 10): $R_t$=3.39 min.

MS (ESIpos): m/z=323 [M+H]$^+$.

$^1$H-NMR (300 MHz, DMSO-d$_6$): δ=1.10 (m, 2H), 1.43 (m, 4H), 1.62 (m, 2H), 2.04 (m, 1H), 2.10 (s, 3H), 2.24 (s, 3H), 2.36 (d, 2H), 6.98 (m, 1H), 7.09 (m, 2H), 9.15 (br. s, 1H), 12.19 (br. s, 1H).

EXAMPLE 9

2-(Cyclopentylmethyl)-4-[(2-methoxyphenyl)amino]-6-oxo-1,6-dihydro-5-pyrimidinecarbonitrile

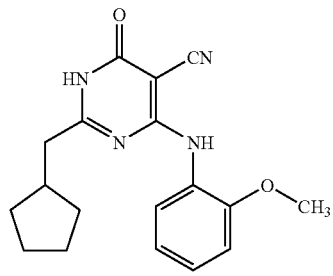

In analogy to the preparation of Example 4, 62 mg (26% of theory) of the title compound are obtained as a colorless solid from 0.2 g (0.71 mmol) of methyl 2-cyano-3-[(2-methoxyphenyl)amino]-3-(methylsulfanyl)-2-propenoate, 0.13 g (0.79 mmol) of 2-cyclopentylethanamidine hydrochloride and 0.22 g (1.58 mmol) of potassium carbonate.

LC-MS (method 1): $R_t$=2.92 min.

MS (ESIpos): m/z=325 [M+H]$^+$.

EXAMPLE 10

2-(Cyclopentylmethyl)-4-[(4-fluoro-2-methylphenyl)amino]-6-oxo-1,6-dihydro-5-pyrimidinecarbonitrile

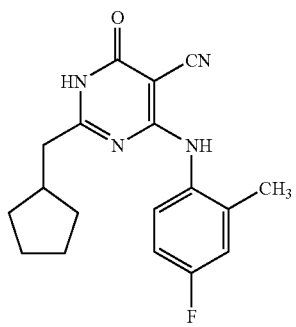

In analogy to the preparation of Example 4, 54 mg (46% of theory) of the title compound are obtained as a colorless solid from 0.1 g (0.36 mmol) of methyl 2-cyano-3-[(4-fluoro-2-methylphenyl)amino]-3-(methylsulfanyl)-2-propenoate, 0.06 g (0.39 mmol) of 2-cyclopentylethanamidine hydrochloride and 0.1 g (0.78 mmol) of potassium carbonate.

LC-MS (method 3): $R_t$=2.98 min.

MS (ESIpos): m/z=327 [M+H]$^+$.

$^1$H-NMR (300 MHz, DMSO-d$_6$): δ=1.09 (m, 2H), 1.53 (m, 6H), 2.10 (m, 1H), 2.14 (s, 3H), 2.28 (d, 2H), 6.98 (m, 1H), 7.08 (m, 1H), 7.29 (m, 1H).

EXAMPLE 11

2-(Cyclopentylmethyl)-4-[(2-methylphenyl)amino]-6-oxo-1,6-dihydro-5-pyrimidinecarbonitrile

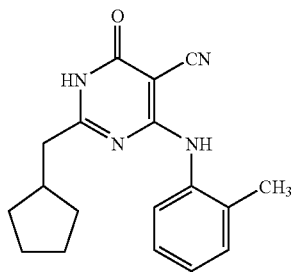

In analogy to the preparation of Example 4, 1.25 g (43% of theory) of the title compound are obtained as a colorless solid from 2.48 g (9.45 mmol) of methyl 2-cyano-3-[(2-methylphenyl)amino]-3-(methylsulfanyl)-2-propenoate, 1.69 g (10.33 mmol) of 2-cyclopentylethanamidine hydrochloride and 2.87 g (20.79 mmol) of potassium carbonate.

LC-MS (method 1): $R_t$=2.84 min.

MS (ESIpos): m/z=309 [M+H]$^+$.

¹H-NMR (300 MHz, DMSO-d₆): δ=1.07 (m, 2H), 1.42 (m, 2H), 1.52 (m, 2H), 1.59 (m, 2H), 2.05 (m, 1H), 2.14 (s, 3H), 2.36 (d, 2H), 7.17 (m, 4H), 9.47 (s, 1H), 12.24 (s, 1H).

EXAMPLE 12

2-(Cyclopentylmethyl)-6-oxo-4-[(2-propylphenyl)amino]-1,6-dihydro-5-pyrimidinecarbonitrile

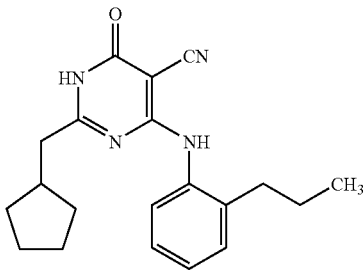

In analogy to the preparation of Example 4, 57 mg (49% of theory) of the title compound are obtained as a colorless solid from 0.1 g (0.34 mmol) of methyl 2-cyano-3-(methylsulfanyl)-3-[(2-propylphenyl)amino]-2-propenoate, 0.06 g (0.37 mmol) of 2-cyclopentylethanamidine hydrochloride and 0.1 g (0.76 mmol) of potassium carbonate.

LC-MS (method 1): $R_t$=3.13 min.

MS (ESIpos): m/z=337 [M+H]⁺.

¹H-NMR (300 MHz, DMSO-d₆): δ=0.84 (t, 3H), 1.07 (m, 2H), 1.52 (m, 8H), 2.04 (m, 1H), 2.35 (d, 2H), 2.49 (m, 2H), 7.16 (m, 2H), 7.23 (m, 2H), 9.44 (s, 1H), 12.20 (s, 1H).

EXAMPLE 13

2-(Cyclopentylmethyl)-6-oxo-4-(3-pyridinylamino)-1,6-dihydro-5-pyrimidinecarbonitrile

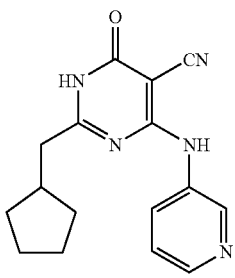

0.1 g (0.40 mmol) of methyl 2-cyano-3-(methylsulfanyl)-3-(3-pyridinylamino)-2-propenoate and 0.065 g (0.40 mmol) of 2-cyclopentylethanamidine hydrochloride and 0.16 g (1.60 mmol) of triethylamine are dissolved in 0.5 ml of DMF and stirred at 100° C. overnight. After cooling, the mixture is diluted with 10 ml of water and extracted with dichloromethane. The organic phase is dried over sodium sulfate and concentrated in vacuo, and the residue is purified by flash chromatography (mobile phase: dichloromethane/methanol 200:1, 100:1, 50:1). 78 mg (64% of theory) of the product are obtained as a colorless solid.

HPLC (method 8): $R_t$=3.36 min.

MS (ESIpos): m/z=296 [M+H]⁺.

¹H-NMR (300 MHz, DMSO-d₆): δ=1.05-1.20 (m, 2H), 1.37-1.75 (m, 6H), 2.16 (m, 1H), 2.47 (d, 2H), 7.36 (m, 1H), 7.83 (m, 1H), 8.32 (m, 1H), 8.66 (m, 1H), 9.80 (s, 1H), 12.48 (s, 1H).

EXAMPLE 14

2-(2-Methylbutyl)-4-[(2-methylphenyl)amino]-6-oxo-1,6-dihydro-5-pyrimidinecarbonitrile

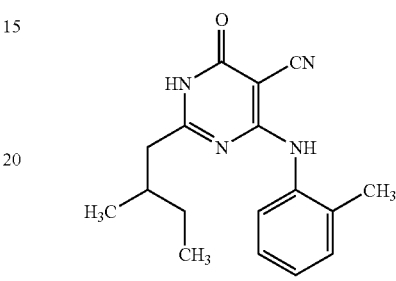

In analogy to the preparation of Example 4, 105 mg (77% of theory) of the title compound are obtained as a colorless solid from 0.12 g (0.46 mmol) of methyl 2-cyano-3-(methylsulfanyl)-3-[(2-methylphenyl)amino]-2-propenoate, 0.07 g (0.50 mmol) of 3-methylpentanamidine hydrochloride and 0.14 g (1.0 mmol) of potassium carbonate.

LC-MS (method 2): $R_t$=2.06 min.

MS (ESIpos): m/z=297 [M+H]⁺.

¹H-NMR (300 MHz, DMSO-d₆): δ=0.80 (d, 6H), 1.09 (m, 1H), 1.24 (m, 1H), 1.74 (m, 1H), 2.14 (s, 3H), 2.32 (dd, 2H), 7.16 (m, 4H), 9.49 (s, 1H), 12.27 (s, 1H).

EXAMPLE 15

2-[(2S)-2-methylbutyl]-4-(2-methylphenyl)amino]-6-oxo-1,6-dihydro-5-pyrimidinecarbonitrile

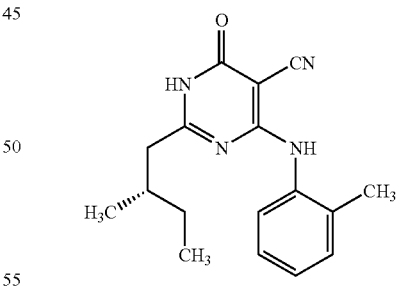

In analogy to the preparation of Example 4, 183 mg (80% of theory) of the title compound are obtained as a colorless solid from 0.2 g (0.76 mol) of methyl 2-cyano-3-(methylsulfanyl)-3-[(2-methylphenyl)amino]-2-propenoate, 0.17 g (1.14 mmol) of (3S)-3-methylpentanamidine hydrochloride and 0.23 g (1.66 mmol) of potassium carbonate.

LC-MS (method 5): $R_t$=2.28 min.

MS (ESIpos): m/z=297 [M+H]⁺.

¹H-NMR (300 MHz, DMSO-d6): δ=0.78 (d, 6H), 1.09 (m, 1H), 1.21 (m, 1H), 1.70 (m, 1H), 2.13 (s, 3H), 2.29 (dd, 2H), 7.16 (m, 4H), 9.49 (s, 1H), 12.25 (s, 1H).

EXAMPLE 16

4-[(5-Fluoro-2-methylphenyl)amino]-2-[(2S)-2-methylbutyl]-6-oxo-1,6-dihydro-5-pyrimidinecarbonitrile

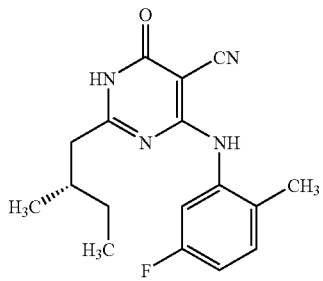

In analogy to the preparation of Example 4, 182 mg (73% of theory) of the title compound are obtained as a colorless solid from 0.22 g (0.78 mmol) of methyl 2-cyano-3-[(5-fluoro-2-methylphenyl)amino]-3-(methylsulfanyl)-2-propenoate, 0.17 g (1.17 mmol) (3S)-3-methylpentanamidine hydrochloride and 0.24 g (1.73 mmol) of potassium carbonate.

LC-MS (method 5): $R_t$=2.11 min.

MS (ESIpos): m/z=315 [M+H]$^+$.

$^1$H-NMR (200 MHz, DMSO-d$_6$): δ=0.75 (d, 6H), 1.1 (m, 1H), 1.25 (m, 1H), 1.71 (m, 1H), 2.1 (s, 3H), 2.26 (dd, 2H), 7.03 (m, 2H), 7.28 (m, 1H), 9.51 (s, 1H), 12.36 (s, 1H).

Examples 17-58 listed in the table below are prepared in analogy to the preparation of Example 4:

| Example | Structure | MS: m/z [M + H]$^+$ | $R_t$ [min] | HPLC or LC-MS method |
|---|---|---|---|---|
| 17 | 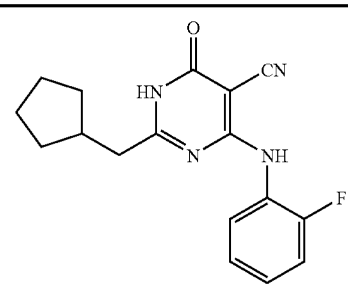 | 313 | 4.37 | 8 |
| 18 | 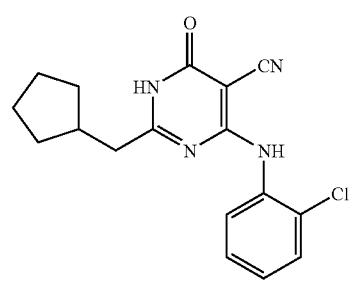 | 329 | 4.52 | 8 |
| 19 | 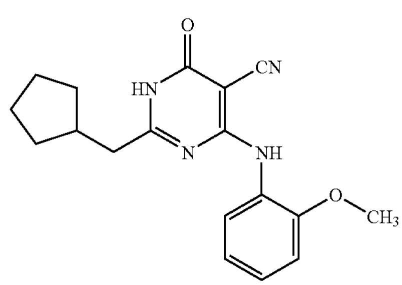 | 325 | 4.50 | 8 |

-continued

| Example | Structure | MS: m/z [M + H]+ | R$_t$ [min] | HPLC or LC-MS method |
|---|---|---|---|---|
| 20 | 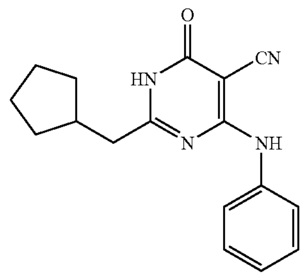 | 295 | 4.39 | 8 |
| 21 | 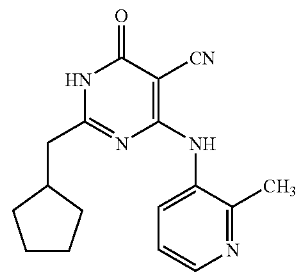 | 310 | 1.82 | 1 |
| 22 | 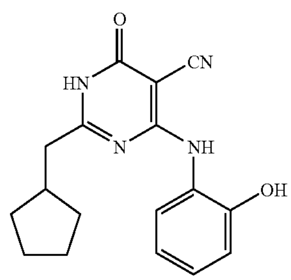 | 311 | 2.75 | 7 |
| 23 | 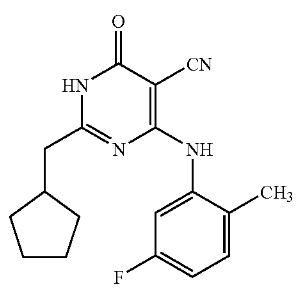 | 327 | 2.39 | 6 |
| 24 | 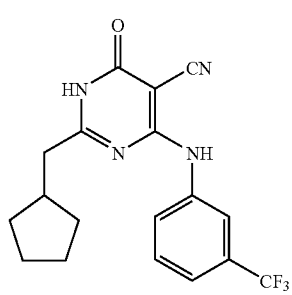 | 363 | 3.12 | 1 |

-continued

| Example | Structure | MS: m/z [M + H]+ | R$_t$ [min] | HPLC or LC-MS method |
|---|---|---|---|---|
| 25 | (structure) | 338 | 2.87 | 10 |
| 26 | (structure) | 325 | 2.78 | 1 |
| 27 | (structure) | 309 | 2.97 | 1 |
| 28 | (structure) | 298 | 1.26 | 2 |

-continued

| Example | Structure | MS: m/z [M + H]+ | R_t [min] | HPLC or LC-MS method |
|---|---|---|---|---|
| 29 | (structure) | 315 | 2.26 | 6 |
| 30 | (structure) | 327 | 4.52 | 8 |
| 31 | (structure) | 341 | 2.51 | 6 |
| 32 | (structure) | 341 | 2.48 | 6 |
| 33 | (structure) | 343 | 4.67 | 8 |

-continued

| Example | Structure | MS: m/z [M + H]+ | Rt [min] | HPLC or LC-MS method |
|---|---|---|---|---|
| 34 | 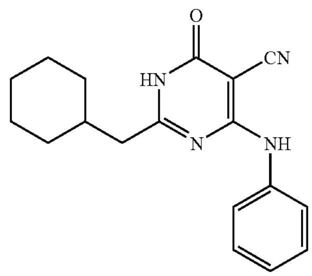 | 309 | 4.55 | 8 |
| 35 | 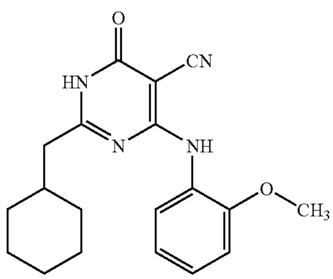 | 339 | 4.67 | 8 |
| 36 | 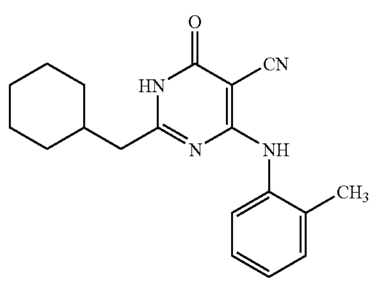 | 340 ([M + NH4]+) | 4.61 | 8 |
| 37 | 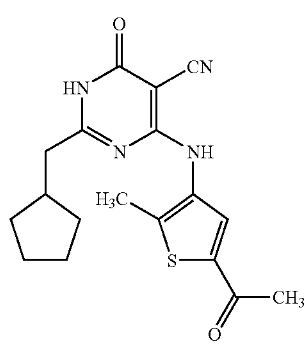 | 357 | 2.7 | 1 |
| 38 | 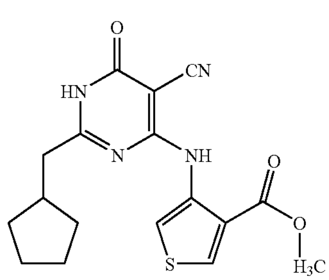 | 359 | 3.3 | 7 |

-continued

| Example | Structure | MS: m/z [M + H]+ | R_t [min] | HPLC or LC-MS method |
|---|---|---|---|---|
| 39 | 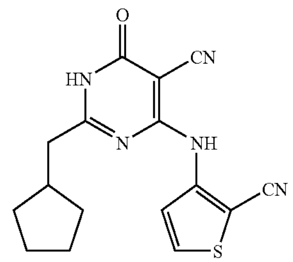 | 326 | 2.23 | 9 |
| 40 | 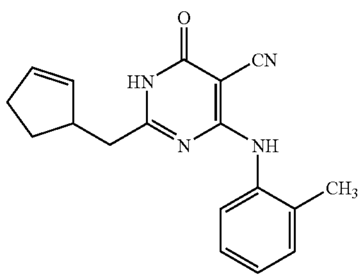 | 307 | 4.35 | 8 |
| 41 | 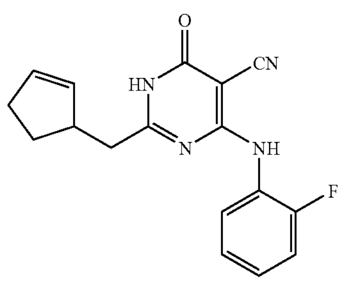 | 311 | 4.25 | 8 |
| 42 | 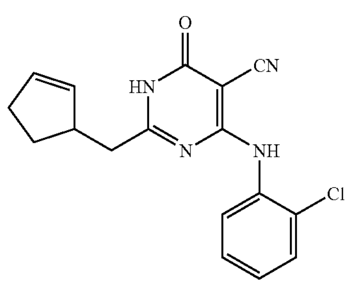 | 327 | 4.40 | 8 |
| 43 | 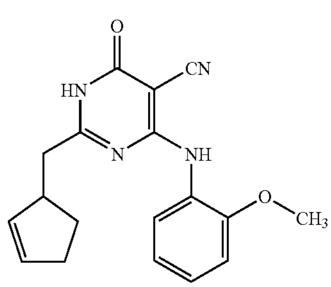 | 323 | 4.39 | 8 |

-continued
| Example | Structure | MS: m/z [M + H]+ | R_t [min] | HPLC or LC-MS method |
|---|---|---|---|---|
| 44 | 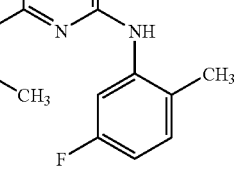 | 315 | 2.34 | 6 |
| 45 | 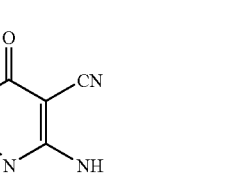 | 339 | 2.3 | 2 |
| 46 | 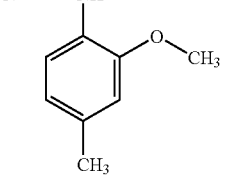 | 323 | 2.18 | 2 |
| 47 | 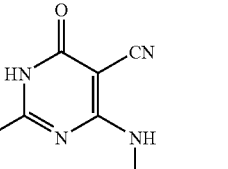 | 337 | 2.31 | 2 |
| 48 | 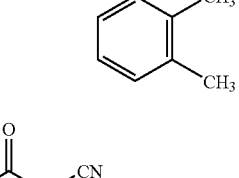 | 355 | 2.09 | 2 |

-continued

| Example | Structure | MS: m/z [M + H]+ | R$_t$ [min] | HPLC or LC-MS method |
|---|---|---|---|---|
| 49 | 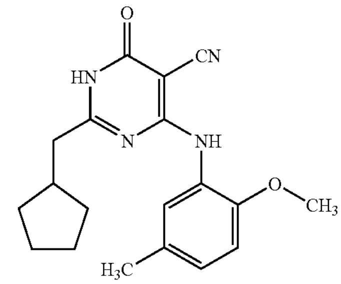 | 339 | 2.33 | 2 |
| 50 | 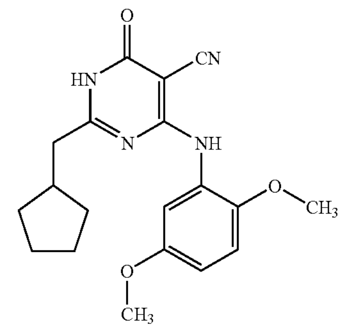 | 355 | 2.20 | 2 |
| 51 | 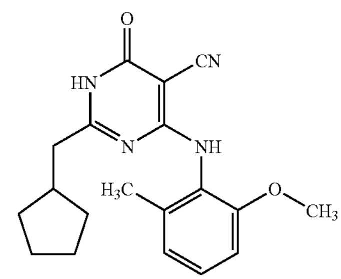 | 339 | 2.05 | 2 |
| 52 | 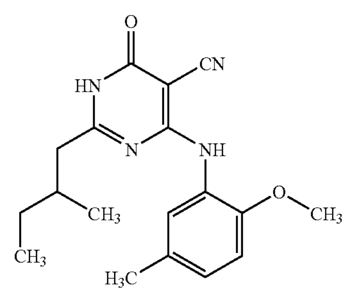 | 327 | 2.48 | 5 |
| 53 | 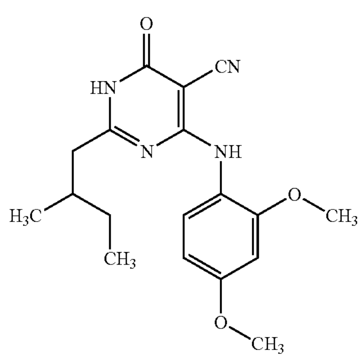 | 343 | 2.25 | 5 |

-continued

| Example | Structure | MS: m/z [M + H]+ | R_t [min] | HPLC or LC-MS method |
|---|---|---|---|---|
| 54 | 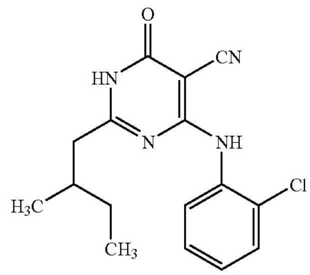 | 317 | 2.32 | 5 |
| 55 | 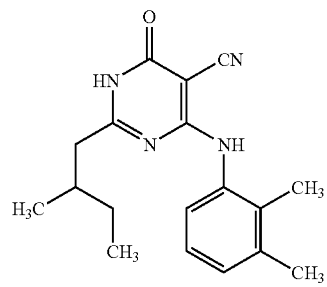 | 311 | 2.34 | 5 |
| 56 | 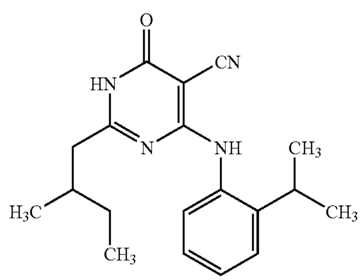 | 325 | 2.26 | 2 |
| 57 | 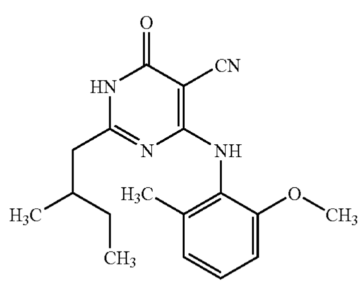 | 327 | 2.23 | 5 |
| 58 | 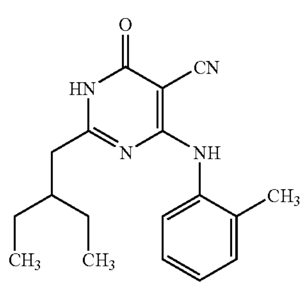 | 311 | 2.40 | 5 |

| Example | Structure | MS: m/z [M + H]+ | R_t [min] | HPLC or LC-MS method |
|---|---|---|---|---|
| 59 | 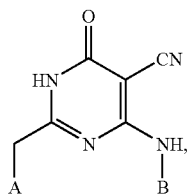 | 297 | 4.40 | 8 |

The invention claimed is:

1. A compound of formula (I)

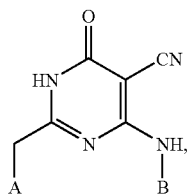

in which

A is $C_1$-$C_8$-alkyl, $C_3$-$C_8$-cycloalkyl, tetrahydrofuryl or tetrahydropyranyl, which are optionally substituted by up to 3 radicals independently of one another selected from the group of $C_1$-$C_6$-alkyl, $C_1$-$C_6$-alkoxy, hydroxycarbonyl, cyano, trifluoromethyl, trifluoromethoxy, amino, hydroxy, $C_1$-$C_6$-alkylamino, halogen, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio, where $C_1$-$C_6$-alkyl, $C_1$-$C_6$-alkoxy, $C_1$-$C_6$-alkylamino, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio are optionally substituted by one or more radicals selected from the group of hydroxy, cyano, halogen, hydroxycarbonyl and a group of the formula —$NR^3R^4$, where $R^3$ and $R^4$ are independently of one another hydrogen or $C_1$-$C_6$-alkyl, or $R^3$ and $R^4$ together with the nitrogen atom to which they are bonded are 5- to 8-membered heterocyclyl, B is phenyl or heteroaryl which are optionally substituted by up to 3 radicals independently of one another selected from the group of $C_1$-$C_6$-alkyl, $C_1$-$C_6$-alkoxy, hydroxycarbonyl, cyano, trifluoromethyl, trifluoromethoxy, amino, nitro, hydroxy, $C_1$-$C_6$-alkylamino, halogen, $C_1$-$C_6$-alkylaminocarbonyl, $C_1$-$C_6$-alkoxycarbonyl, $C_1$-$C_6$-alkylcarbonyl, $C_1$-$C_6$-alkylsulfonyl and $C_1$-$C_6$-alkylthio, where $C_1$-$C_6$-alkyl, $C_1$-$C_6$-alkoxy, $C_1$-$C_6$-alkylamino, $C_1$-$C_6$-alkylaminocar-bonyl, $C_1$-$C_6$-alkoxycarbonyl, $C_1$-$C_6$-alkylcarbonyl, $C_1$-$C_6$-alkylsul-fonyl and $C_1$-$C_6$-alkylthio are optionally substituted by a radical selected from the group of hydroxy, cyano, halogen, hydroxycarbonyl and a group of the formula —$NR^3R^4$, where $R^3$ and $R^4$ have the abovementioned meanings, or salts thereof.

2. A compound as claimed in claim 1, where

A is $C_1$-$C_5$-alkyl or $C_3$-$C_6$-cycloalkyl, which are optionally substituted by up to 3 radicals independently of one another selected from the group of $C_1$-$C_4$-alkyl, $C_1$-$C_4$-alkoxy, hydroxycarbonyl, cyano, amino, hydroxy, $C_1$-$C_4$-alkylamino, fluorine, chlorine, bromine, $C_1$-$C_4$-alkoxycarbonyl, $C_1$-$C_6$-alkylcarbonyl, $C_1$-$C_4$-alkylsulfonyl and $C_1$-$C_4$-alkylthio, where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$, where $R^3$ and $R^4$ are independently of one another hydrogen or $C_1$-$C_4$-alkyl, or $R^3$ $R^4$ together with the nitrogen atom to which they are bonded are 5- to 6-membered heterocyclyl, B is phenyl, thienyl or pyridyl, which are optionally substituted by up to 3 radicals in each case independently of one another selected from the group of $C_1$-$C_4$-alkyl, $C_1$-$C_4$-alkoxy, hydroxycarbonyl, cyano, trifluoromethyl, trifluoro-methoxy, amino, hydroxy, $C_1$-$C_4$-alkylamino, fluorine, chlorine, bromine, $C_1$-$C_4$-alkylaminocarbonyl, $C_1$-$C_4$-alkoxycarbonyl, $C_1$-$C_4$-alkylcarbonyl, $C_1$-$C_4$-alkylsulfonyl and $C_1$-$C_4$-alkylthio, where $C_1$-$C_4$-alkyl and $C_1$-$C_4$-alkoxy are optionally substituted by a radical selected from the group of hydroxy, cyano, fluorine, chlorine, bromine, hydroxycarbonyl and a group of the formula —$NR^3R^4$, where $R^3$ and $R^4$ have the abovementioned meanings, or salts thereof.

3. A compound as claimed in claim 1, where

A is $C_3$-$C_5$-alkyl or $C_5$-$C_6$-cycloalkyl,

B is phenyl, thienyl or pyridyl, which are optionally substituted by up to 3 radicals in each case independently of one another selected from the group of $C_1$-$C_3$-alkyl, trifluoromethyl, hydroxy, methoxy, ethoxy, cyano, dimethylamino, diethylamino, methoxycarbonyl, ethoxycarbonyl, methylcarbonyl, ethylcarbonyl, fluorine and chlorine, or salts thereof.

4. A process for preparing compounds of formula (I), characterized in that compounds of formula

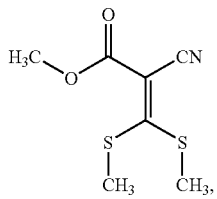

(II)

are initially converted with a compound of the formula

(III)

in which

B has the meaning stated in claim 1, at elevated temperature in an inert solvent or else in the absence of a solvent into a compound of formula

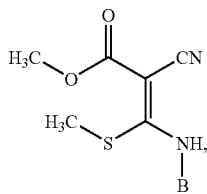

(IV)

in which

B has the meaning stated in claim 1, and the latter is then reacted in an inert solvent in the presence of a base with a compound of formula

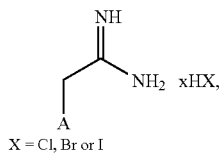

(V)

X = Cl, Br or I in which

A has the meaning stated in claim 1, and the resulting compounds of formula (I) are reacted where appropriate with the appropriate (i) solvents and/or (ii) bases or acids to give their salts.

5. A medicament comprising at least one of the compounds as claimed in any claims 1 to 3 and at least one pharmaceutically acceptable, essentially non-toxic carrier or excipient.

6. A method for improving learning and/or memory comprising administering to a human or animal an effective amound of a compound of claims 1 to 3.

7. A method for treating impairments of learning and/or memory in humans or animals comprising administering to a human or animal an effective amount of a compound of claims 1 to 3.

8. The method as claimed in claim 7, where the impairment is a consequence of Alzheimer's disease.

* * * * *